US010426420B2

(12) United States Patent
Arai et al.

(10) Patent No.: US 10,426,420 B2
(45) Date of Patent: Oct. 1, 2019

(54) MAMMOGRAPHY APPARATUS, CONTROL DEVICE, MAMMOGRAPHY APPARATUS CONTROL METHOD, AND MAMMOGRAPHY APPARATUS CONTROL PROGRAM

(71) Applicant: FUJIFILM CORPORATION, Minato-ku, Tokyo (JP)

(72) Inventors: Takahisa Arai, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 256 days.

(21) Appl. No.: 15/624,725

(22) Filed: Jun. 16, 2017

(65) Prior Publication Data
US 2017/0367671 A1    Dec. 28, 2017

(30) Foreign Application Priority Data

Jun. 22, 2016  (JP) .................................. 2016-123931

(51) Int. Cl.
*A61B 6/04*    (2006.01)
*A61B 6/00*    (2006.01)

(52) U.S. Cl.
CPC .............. *A61B 6/502* (2013.01); *A61B 6/00* (2013.01); *A61B 6/0414* (2013.01); *A61B 6/44* (2013.01); *A61B 6/544* (2013.01)

(58) Field of Classification Search
CPC ....... A61B 6/547; A61B 6/502; A61B 6/0414; A61B 6/44; A61B 6/461; A61B 6/544; A61B 6/00
See application file for complete search history.

(56) References Cited

U.S. PATENT DOCUMENTS 5,922,018 A * 7/1999 Sarvazyan ........... A61B 1/0052
                                                          600/587
9,020,094 B2   4/2015 Popova et al.
(Continued)

FOREIGN PATENT DOCUMENTS

JP    H06-261896 A    9/1994
JP    2009-077969 A   4/2009
(Continued)

OTHER PUBLICATIONS

English language translation of the following: Office action dated May 7, 2019 from the JPO in a Japanese patent application No. 2016-123931 corresponding to the instant patent application.
(Continued)

*Primary Examiner* — Kiho Kim
(74) *Attorney, Agent, or Firm* — SOLARIS Intellectual Property Group, PLLC

(57) ABSTRACT

A mammography apparatus includes: a moving unit that moves a compression plate in a compression direction in which the breast is compressed and a decompression direction in which the breast is decompressed; a radiation source; a pressure sensor that is used to measure a compression pressure which is a compression force of the compression plate per unit area; and a control unit that controls the moving unit such that the compression plate is moved to a first position where the compression pressure measured by the pressure sensor is a first compression pressure in the compression direction and is moved to a second position where the compression pressure measured by the pressure sensor is a second compression pressure in the decompression direction and performs control such that radiation is emitted from the radiation source in a state in which the compression plate is located at the second position.

24 Claims, 34 Drawing Sheets

(56) References Cited

U.S. PATENT DOCUMENTS

| | | | |
|---|---|---|---|
| 10,238,343 B2* | 3/2019 | Goossen | A61B 6/0414 |
| 2002/0004630 A1* | 1/2002 | Sarvazyan | A61B 5/0053 |
| | | | 600/372 |
| 2007/0221859 A1 | 9/2007 | Nakata | |
| 2008/0080674 A1 | 4/2008 | Kashiwagi | |
| 2008/0087830 A1 | 4/2008 | Kashiwagi | |
| 2009/0220055 A1 | 9/2009 | Nakata et al. | |
| 2009/2020055 | 9/2009 | Nakata et al. | |
| 2010/0054557 A1 | 3/2010 | Morita et al. | |
| 2010/0113970 A1 | 5/2010 | Okada | |
| 2010/0208958 A1 | 8/2010 | Yamada et al. | |
| 2010/0246921 A1 | 9/2010 | Iwami et al. | |
| 2012/0014504 A1 | 1/2012 | Jang et al. | |
| 2012/0014505 A1 | 1/2012 | Morita et al. | |
| 2012/0014585 A1 | 1/2012 | Morita et al. | |
| 2012/0020464 A1 | 1/2012 | Matsuura | |
| 2012/0053456 A1* | 3/2012 | Hoernig | A61B 6/00 |
| | | | 600/431 |
| 2012/0157819 A1 | 6/2012 | Jerebko et al. | |
| 2013/0068952 A1 | 3/2013 | Kuwabara | |
| 2013/0237859 A1* | 9/2013 | Taku | A61B 5/0091 |
| | | | 600/476 |
| 2013/0301799 A1 | 11/2013 | Kang et al. | |
| 2014/0072100 A1 | 3/2014 | Jang et al. | |
| 2014/0093033 A1 | 4/2014 | Takata et al. | |
| 2014/0093034 A1* | 4/2014 | Takata | A61B 6/544 |
| | | | 378/37 |
| 2014/0328458 A1 | 11/2014 | Erhard et al. | |
| 2014/0341338 A1* | 11/2014 | Grimbergen | A61B 6/0414 |
| | | | 378/37 |
| 2015/0003579 A1* | 1/2015 | Kim | A61B 6/502 |
| | | | 378/37 |
| 2015/0036796 A1 | 2/2015 | Dornberger et al. | |
| 2015/0093013 A1 | 4/2015 | Morita | |
| 2015/0157282 A1* | 6/2015 | Kobayashi | A61B 6/502 |
| | | | 378/37 |
| 2015/0164426 A1* | 6/2015 | Goossen | A61B 6/0414 |
| | | | 600/415 |
| 2015/0297163 A1* | 10/2015 | Kim | A61B 6/5217 |
| | | | 378/37 |
| 2015/0327829 A1 | 11/2015 | Morita | |
| 2016/0000386 A1 | 1/2016 | Souchay et al. | |
| 2016/0166234 A1 | 6/2016 | Zhang et al. | |
| 2016/0235379 A1* | 8/2016 | Homann | A61B 6/502 |
| 2016/0278730 A1 | 9/2016 | Moon | |
| 2017/0265828 A1* | 9/2017 | Tsujii | A61B 6/502 |

FOREIGN PATENT DOCUMENTS

| | | |
|---|---|---|
| JP | 2011-206434 A | 10/2011 |
| JP | 2014-068884 A | 4/2014 |
| JP | 2014-533548 A | 12/2014 |
| JP | 2016-514538 A | 5/2016 |
| KR | 20140104267 A | 8/2014 |

OTHER PUBLICATIONS

Extended European Search Report dated Nov. 30, 2017, issued in corresponding EP Patent Application No. 17176637.1.
Non-Final Office Action issued by USPTO dated Apr. 15, 2019, in related U.S. Appl. No. 15/623,405.
Non-Final Office Action issued by USPTO dated Apr. 25, 2019, in related U.S. Appl. No. 15/624,726.
English language translation of the following: Office action dated May 7, 2019 from the JPO in a Japanese patent application No. 2016-123930 corresponding to the instant patent application.
English language translation of the following: Office action dated Jun. 4, 2019 from the JPO in a Japanese patent application No. 2016-123932 corresponding to the instant patent application.

* cited by examiner

FIG. 13A

| THICKNESS | SECOND COMPRESSION PRESSURE |
|---|---|
| LARGE | $0.016 N/mm^2$ |
| NORMAL | $0.014 N/mm^2$ |
| SMALL | $0.012 N/mm^2$ |

| THICKNESS | DIFFERENCE FROM REFERENCE VALUE |
|---|---|
| LARGE | $+0.002 N/mm^2$ |
| NORMAL | 0 |
| SMALL | $-0.002 N/mm^2$ |

| THICKNESS | PERCENTAGE WITH RESPECT TO REFERENCE VALUE |
|---|---|
| LARGE | 115% |
| NORMAL | 100% |
| SMALL | 85% |

| CUP | SECOND COMPRESSION PRESSURE |
|---|---|
| AB | $0.012 N/mm^2$ |
| CD | $0.014 N/mm^2$ |
| EQUAL TO OR LARGER THAN E | $0.016 N/mm^2$ |

| SIZE | SECOND COMPRESSION PRESSURE | 43C |
|---|---|---|
| LARGE | 0.016N/mm$^2$ | |
| MEDIUM | 0.014N/mm$^2$ | |
| SMALL | 0.012N/mm$^2$ | |

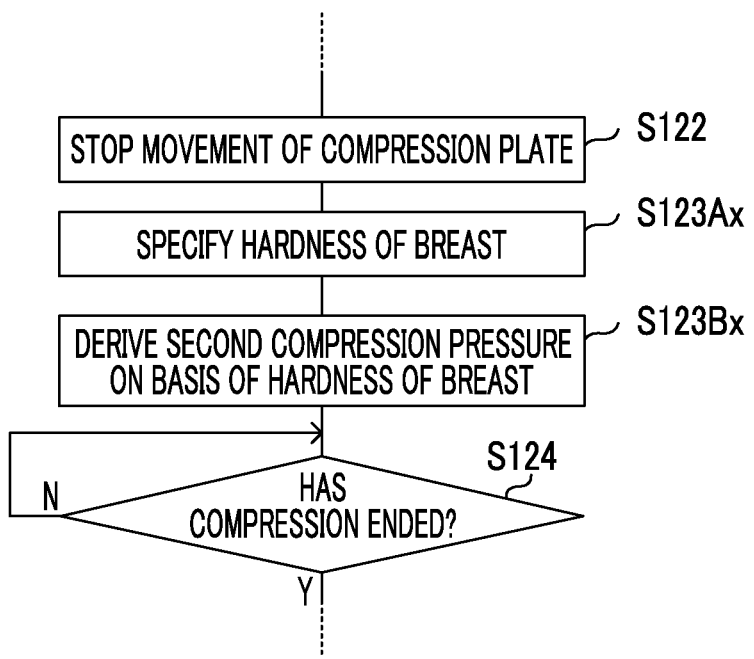

FIG. 27

| WEIGHT | SECOND COMPRESSION PRESSURE (43F) |
|---|---|
| LARGE | $0.016 N/mm^2$ |
| NORMAL | $0.014 N/mm^2$ |
| SMALL | $0.012 N/mm^2$ |

| THICKNESS | SECOND COMPRESSION PRESSURE | SECOND MOVING SPEED |
|---|---|---|
| LARGE | 0.016N/mm² | 0.5mm/s |
| NORMAL | 0.014N/mm² | 1mm/s |
| SMALL | 0.012N/mm² | 1.5mm/s |

43A4

| | COMPRESSION PRESSURE | THICKNESS OF BREAST |
|---|---|---|
| FIRST COMPRESSION : | 0.027N/mm² | 45mm |
| SECOND COMPRESSION : | | |
| CURRENT VALUE : | 0.020N/mm² | 46mm |

MAMMOGRAPHY APPARATUS, CONTROL DEVICE, MAMMOGRAPHY APPARATUS CONTROL METHOD, AND MAMMOGRAPHY APPARATUS CONTROL PROGRAM

CROSS-REFERENCE TO RELATED APPLICATION

This application claims priority under 35 USC 119 from Japanese Patent Application No. 2016-123931 filed on Jun. 22, 2016, the disclosure of which is incorporated by reference herein.

BACKGROUND OF THE INVENTION

1. Field of the Invention

The present invention relates to a mammography apparatus, a control device, a mammography apparatus control method, and a mammography apparatus control program.

2. Description of the Related Art

A mammography apparatus has been known which captures a radiographic image of the breast of a subject. In a case in which the mammography apparatus captures a radiographic image of the breast of the subject, the breast is compressed by a compression plate.

In a case in which the breast is compressed by the compression plate, in many cases, the subject feels a pain since the breast is squeezed or extended. As a result, the subject feels some pressure.

JP1994-261896A (JP-H06-261896A) discloses a technique that prevents the subject's pain. In the technique disclosed in JP1994-261896A (JP-H06-261896A), in a case in which a variation in the thickness of the breast is less than a predetermined value, when a compression force applied to the breast increases, the subject's pain increases and the quality of a radiographic image is not improved.

Therefore, the compression force is adjusted according to the thickness of the breast such that an increase in the compression force is stopped. In this way, it is possible to prevent the subject's pain caused by an increase in the compression force.

SUMMARY OF THE INVENTION

However, in the technique disclosed in JP1994-261896A (JP-H06-261896A), it is possible to prevent the pain in a case in which the compression force continues to increase. However, the pain persists at the time when an increase in the compression force is stopped. Therefore, this technique is insufficient to reduce the pain caused by the continuous compression of the breast.

The invention has been made in view of the above-mentioned problems and an object of the invention is to provide a mammography apparatus, a control device, a mammography apparatus control method, and a mammography apparatus control program that can effectively reduce the subject's pain caused by the compression of the breast by a compression plate.

In order to achieve the object, according to an aspect of the invention, there is provided a mammography apparatus comprising: a compression plate that compresses a breast; a moving unit that moves the compression plate in a compression direction in which the breast is compressed and a decompression direction in which the breast is decompressed; a radiation source that emits radiation; a measurement unit that measures a compression pressure which is a compression force of the compression plate per unit area; and a control unit that controls the moving unit such that the compression plate is moved to a first position where the compression pressure measured by the measurement unit is a first compression pressure in the compression direction and is moved to a second position where the compression pressure measured by the measurement unit is a second compression pressure in the decompression direction and performs control such that the radiation is emitted from the radiation source to the breast in a state in which the compression plate is located at the second position.

In the mammography apparatus according to the above-mentioned aspect of the invention, it is preferable that the first compression pressure is higher than the second compression pressure.

In the mammography apparatus according to the above-mentioned aspect of the invention, the control unit may further perform control such that a measurement result of the measurement unit is displayed on a display unit.

The mammography apparatus according to the above-mentioned aspect of the invention may further comprise a storage unit that stores the first compression pressure and the second compression pressure in advance.

The mammography apparatus according to the above-mentioned aspect of the invention may further comprise a storage unit that stores a plurality of second compression pressure candidates corresponding to the type of breast. The control unit may use a second compression pressure candidate selected from the plurality of second compression pressure candidates as the second compression pressure.

The mammography apparatus according to the above-mentioned aspect of the invention may further comprise a compression pressure operation unit that is operated to set at least one of the first compression pressure or the second compression pressure.

In the mammography apparatus according to the above-mentioned aspect of the invention, in a case in which the compression pressure operation unit is operated to set the first compression pressure, the control unit may derive the second compression pressure according to the set first compression pressure and the type of breast.

The mammography apparatus according to the above-mentioned aspect of the invention may further comprise a state operation unit that is operated to set the type of breast.

In the mammography apparatus according to the above-mentioned aspect of the invention, the type of breast may include at least one of a thickness of the breast, a cup size of the breast, a size of the breast, a weight of the breast, a hardness of the breast, or mammary gland density.

In the mammography apparatus according to the above-mentioned aspect of the invention, in a case in which the compression pressure operation unit is operated to set one of the first compression pressure and the second compression pressure, the magnitude of a compression pressure that can be set by an operation for the compression pressure operation unit as the other of the first compression pressure and the second compression pressure may be limited.

In the mammography apparatus according to the above-mentioned aspect of the invention, the first compression pressure may be equal to or greater than $0.018$ N/mm$^2$ and the second compression pressure be in the range of $0.009$ N/mm$^2$ to $0.023$ N/mm$^2$.

In the mammography apparatus according to the above-mentioned aspect of the invention, in a case in which a predetermined period of time has elapsed since the compression pressure measured by the measurement unit has reached the first compression pressure, the control unit may control the moving unit such that the movement of the compression plate in the decompression direction starts.

In the mammography apparatus according to the above-mentioned aspect of the invention, in a case in which the compression pressure measured by the measurement unit reaches the first compression pressure, the control unit may control the moving unit such that the movement of the compression plate in the decompression direction starts.

The mammography apparatus according to the above-mentioned aspect of the invention may further comprise a movement instruction operation unit that is operated to input an instruction to move the compression plate to the second position. In a case in which the movement instruction operation unit is operated to input an instruction to move the compression plate, the control unit may control the moving unit such that the movement of the compression plate to the second position starts.

In the mammography apparatus according to the above-mentioned aspect of the invention, in a case in which the compression pressure measured by the measurement unit is equal to or greater than a predetermined value until the compression plate is moved to the first position, the control unit may perform control such that a moving speed of the compression plate is reduced.

The mammography apparatus according to the above-mentioned aspect of the invention may further comprise a contact detection unit that detects whether the compression plate comes into contact with the breast. In a case in which the contact detection unit detects the contact between the compression plate and the breast until the compression plate is moved to the first position, the control unit may perform control such that a moving speed of the compression plate is reduced.

In the mammography apparatus according to the above-mentioned aspect of the invention, the control unit may perform control such that a second moving speed of the compression plate in the decompression direction is lower than a first moving speed of the compression plate in the compression direction.

In the mammography apparatus according to the above-mentioned aspect of the invention, the control unit may perform control such that a second moving speed of the compression plate in the decompression direction is higher than a first moving speed of the compression plate in the compression direction.

In the mammography apparatus according to the above-mentioned aspect of the invention, the control unit may derive the second moving speed according to the type of breast.

The mammography apparatus according to the above-mentioned aspect of the invention may further comprise: a prohibition information storage unit that stores prohibition information indicating the type of compression plate which is prohibited from being moved to the second position in the decompression direction; and a reading unit that reads identification information which identifies the type of compression plate and is provided in the compression plate. The control unit may prohibit control for moving the compression plate to the second position in the decompression direction, on the basis of the type of compression plate which is identified by the identification information read by the reading unit and the prohibition information stored in the prohibition information storage unit.

In order to achieve the object, according to another aspect of the invention, there is provided a control device comprising: a receiving unit that receives a measurement result from a measurement unit that measures a compression pressure which is a compression force of a compression plate compressing a breast per unit area; and a control unit that controls a moving unit that moves the compression plate in a compression direction in which the breast is compressed and a decompression direction in which the breast is decompressed such that the compression plate is moved to a first position where the compression pressure received by the receiving unit is a first compression pressure in the compression direction and is moved to a second position where the compression pressure received by the receiving unit is a second compression pressure in the decompression direction and performs control such that radiation is emitted from a radiation source to the breast in a state in which the compression plate is located at the second position.

In order to achieve the object, according to still another aspect of the invention, there is provided a mammography apparatus control method comprising: receiving a measurement result from a measurement unit that measures a compression pressure which is a compression force of a compression plate compressing a breast per unit area; controlling a moving unit that moves the compression plate in a compression direction in which the breast is compressed and a decompression direction in which the breast is decompressed such that the compression plate is moved to a first position where the received compression pressure is a first compression pressure in the compression direction; controlling the moving unit such that the compression plate is moved to a second position where the received compression pressure is a second compression pressure in the decompression direction; and performing control such that radiation is emitted from a radiation source to the breast in a state in which the compression plate is located at the second position.

In order to achieve the object, according to yet another aspect of the invention, there is provided a mammography apparatus control program that causes a computer to perform a process comprising: receiving a measurement result from a measurement unit that measures a compression pressure which is a compression force of a compression plate compressing a breast per unit area; controlling a moving unit that moves the compression plate in a compression direction in which the breast is compressed and a decompression direction in which the breast is decompressed such that the compression plate is moved to a first position where the received compression pressure is a first compression pressure in the compression direction; controlling the moving unit such that the compression plate is moved to a second position where the received compression pressure is a second compression pressure in the decompression direction; and performing control such that radiation is emitted from a radiation source to the breast in a state in which the compression plate is located at the second position.

The invention can provide a mammography apparatus, a control device, a mammography apparatus control method, and a mammography apparatus control program that can effectively reduce the subject's pain caused by the compression of the breast by a compression plate.

BRIEF DESCRIPTION OF THE DRAWINGS

FIG. 13A is a diagram schematically illustrating an example of information indicating the correspondence relationship between the thickness of the breast and a second compression pressure.

FIG. 13B is a diagram schematically illustrating an example of information indicating the correspondence relationship between the thickness of the breast and a difference between the second compression pressure and a reference value.

FIG. 13C is a diagram schematically illustrating an example of information indicating the correspondence relationship between the thickness of the breast and the percentage of the second compression pressure with respect to the reference value.

FIG. 16 is a diagram schematically illustrating an example of information indicating the correspondence relationship between the thickness of the breast and the second compression pressure.

FIG. 20 is a diagram schematically illustrating an example of information indicating the correspondence relationship between the size of the breast and the second compression pressure.

FIG. 24 is a diagram schematically illustrating an example of information indicating the correspondence relationship between the hardness of the breast and the second compression pressure.

FIG. 25 is a flowchart illustrating an imaging process performed by a mammography apparatus according to a sixth embodiment.

FIG. 27 is a diagram schematically illustrating an example of information indicating the correspondence relationship between the weight of the breast and the second compression pressure.

DESCRIPTION OF THE PREFERRED EMBODIMENTS

Hereinafter, embodiments of the invention will be described in detail with reference to the drawings. These embodiments do not limit the invention.

First Embodiment

Figure 1:
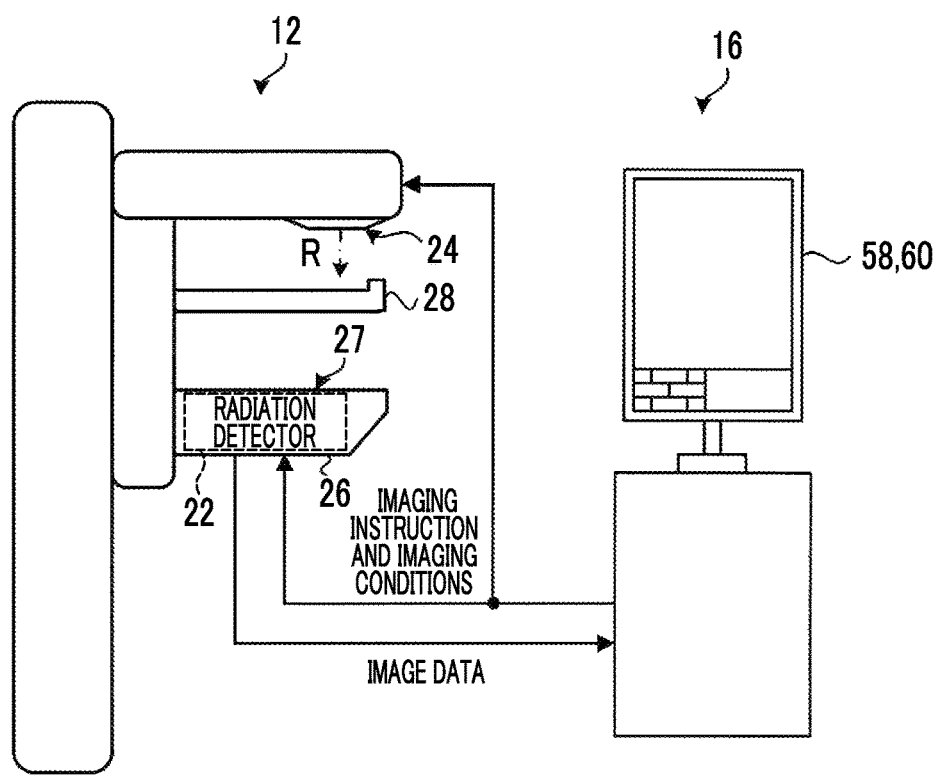
FIG. 1 is a diagram illustrating the structure of a radiography system according to a first embodiment.

First, a radiography system according to this embodiment will be described. FIG. 1 is a diagram illustrating the structure of a radiography system 10 according to this embodiment.

The radiography system 10 according to this embodiment is operated by a user, such as a doctor or a radiological technician, and has a function of capturing radiographic images on the basis of an instruction (imaging menu) which is input from an external system (for example, a radiology information system (RIS)) through a console 16.

The radiography system 10 according to this embodiment comprises a mammography apparatus 12 and the console 16.

The mammography apparatus 12 according to this embodiment captures a radiographic image of the breast of a subject. The mammography apparatus 12 may be an apparatus that captures an image of the breast of the subject in a seated state in which the subject sits down on a chair (including a wheelchair) as well as a state in which the subject stands up or an apparatus that can separately capture at least the images of the left and right breasts of the subject.

The mammography apparatus 12 includes a radiation source 24 that is provided so as to face an imaging surface 27 of an imaging stand 26. Radiation R is emitted from the radiation source 24 to the imaging surface 27.

In a case in which a radiographic image of the breast of the subject is captured, one of the left and right breasts of the subject is compressed and fixed between a compression plate 28 and the imaging stand 26 and the radiation R is emitted from the radiation source 24 to the fixed breast. A radiation detector 22 detects the radiation R that has been emitted and has passed through the breast. A radiographic image of the breast is generated on the basis of the radiation R detected by the radiation detector 22.

Figure 2:
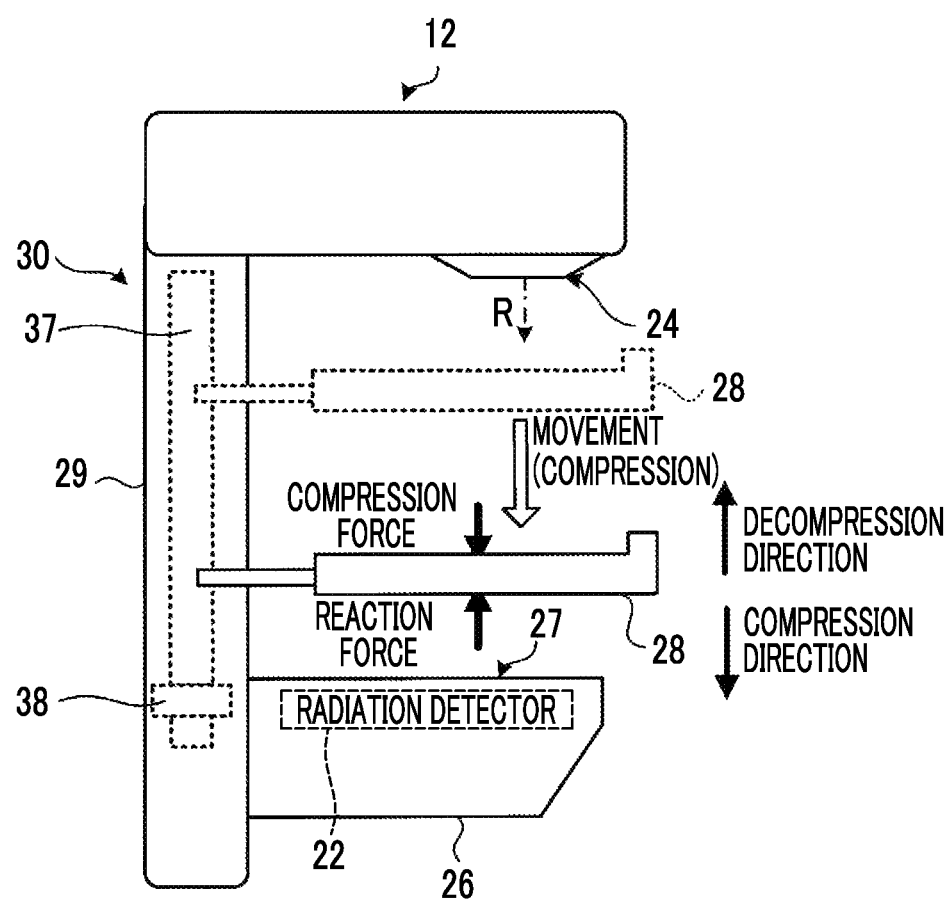
FIG. 2 is a side view illustrating the compression of the breast by a compression plate according to the first embodiment.

FIG. 2 is a side view illustrating the compression of the breast by the compression plate 28 according to this embodiment. The compression plate 28 according to this embodiment is a plate-shaped compression member. In a case in which the breast is compressed, the compression plate 28 compresses the breast from the upper side (the head side of the subject) to the lower side. As illustrated in FIG. 2, hereinafter, for the moving direction of the compression plate 28, a direction in which the breast is compressed is referred to as a "compression direction" and a direction in which the breast is decompressed is referred to as a "decompression direction".

The compression plate 28 is held by a holding portion 29 such that it can be slidably moved between the imaging stand 26 and the radiation source 24 by a moving unit 30 and the gap between the compression plate 28 and the imaging stand 26 is variable. The holding portion 29 comprises the moving unit 30 including a ball screw 37 and a motor 38. The compression plate 28 is supported by the ball screw 37 and the motor 38 is driven to slidably move the compression plate 28 between the imaging stand 26 and the radiation source 24.

A member that transmits the radiation R is used as the compression plate 28. The compression plate 28 according to this embodiment is made of polyethylene terephthalate which is a thermoplastic as a resin material. The material used for the compression plate 28 is not limited thereto. For example, members, such as polycarbonate, acryl, and polypropylene, can be used. The member forming the compression plate 28 is not limited to that in this embodiment. For example, the compression plate 28 may be a film-shaped member.

Figure 3:
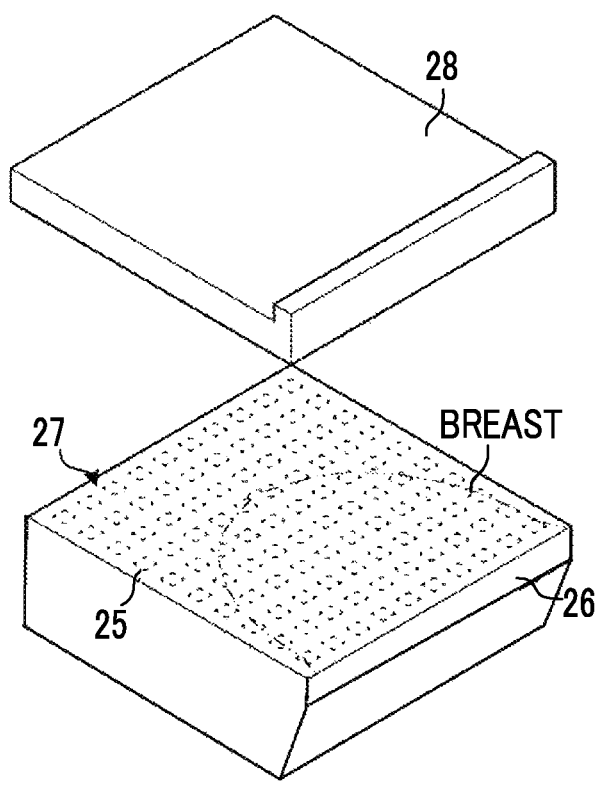
FIG. 3 is a diagram schematically illustrating an example of the state of pressure sensors provided on an imaging surface of an imaging stand.

As illustrated in FIG. 3, n (50 in this embodiment) pressure sensors 25 are two-dimensionally arranged on the imaging surface 27 of the imaging stand 26. Each of the pressure sensors 25 detect pressure generated when the breast is compressed by the compression plate 28 and is pressed against the imaging stand 26. In each of the pressure sensors 25 according to this embodiment, the size of a region for detecting pressure (the area of the imaging surface 27; hereinafter, referred to as a "pressure detection area") is predetermined. In the mammography apparatus 12 according to this embodiment, a control unit 40 derives compression pressure which is a compression force per unit area on the basis of the detection results of the pressure sensors 25, which will be described in detail below, and functions as a measurement unit according to the invention.

It is preferable that the pressure sensor 25 is made of a material which transmits the radiation R. In a case in which the pressure sensor 25 is made of a material that absorbs a portion of the radiation R, the image data of an acquired radiographic image is corrected according to the radiation transmittance of the pressure sensor 25.

The imaging stand 26 includes the radiation detector 22 that is irradiated with the radiation R which has passed through the compression plate 28, the breast, the pressure sensors 25, and the imaging surface 27 and detects the radiation R. The radiation R detected by the radiation detector 22 is visualized and a radiographic image is generated. The radiation detector 22 is irradiated with the radiation R, records image data indicating a radiographic image, and outputs the recorded image data. The radiation detector 22 detects charge in each pixel, which has been generated according to the dose of the emitted radiation R, as image data.

The type of the radiation detector 22 according to this embodiment is not particularly limited. For example, the radiation detector 22 may be an indirect-conversion-type radiation detector that converts the radiation R into light and converts the converted light into charge or a direct-conversion-type radiation detector that directly converts the radiation R into charge.

In this embodiment, the image data indicating the radiographic image which is output from the radiation detector 22 of the mammography apparatus 12 is transmitted to the console 16. The console 16 according to this embodiment has a function of controlling the mammography apparatus 12, using, for example, an imaging menu or various kinds of information acquired from an external system through a wireless communication local area network (LAN).

Figure 4:
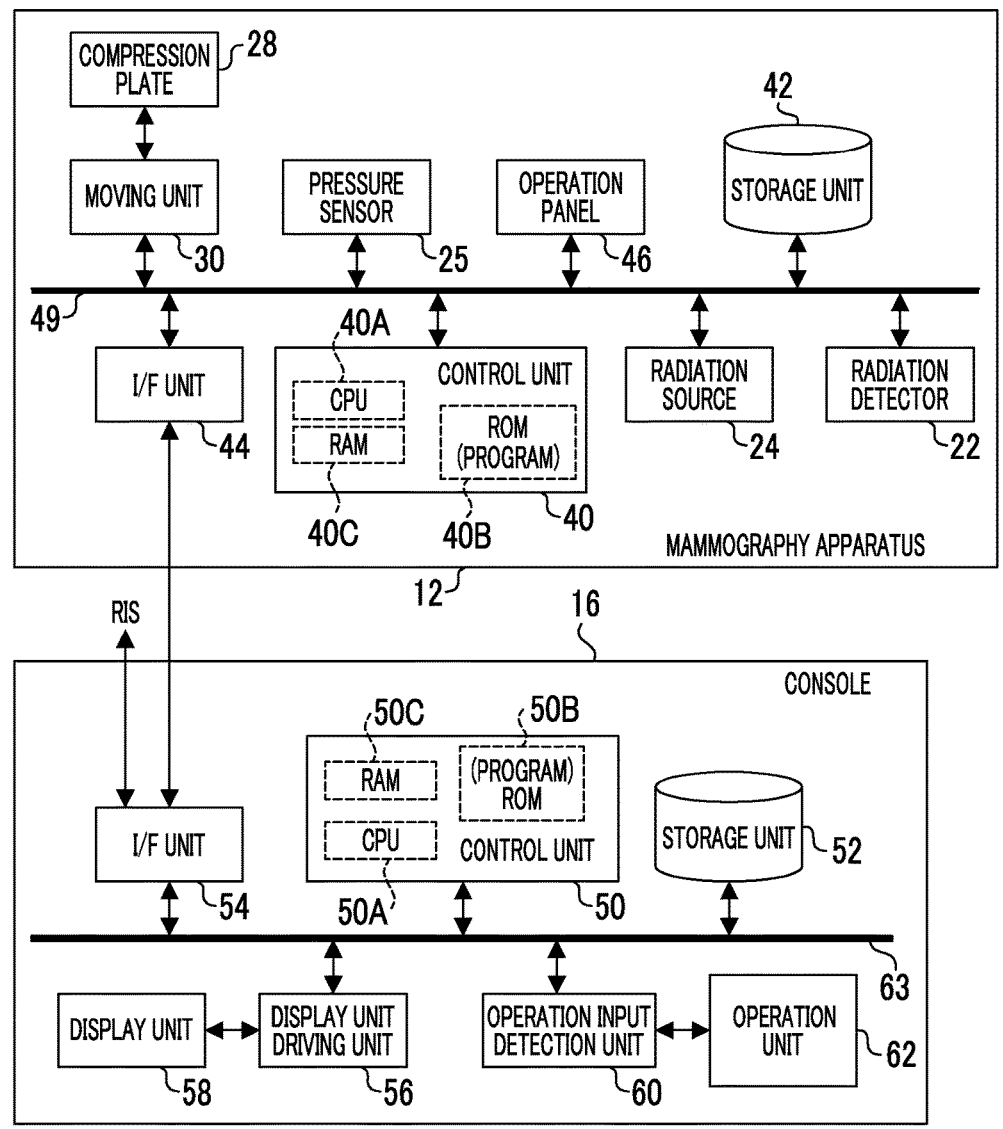
FIG. 4 is a block diagram illustrating the structure of the radiography system according to the first embodiment.

FIG. 4 is a block diagram illustrating the structure of the radiography system 10 according to this embodiment.

The console 16 according to this embodiment is a server computer. As illustrated in FIG. 4, the console 16 comprises a control unit 50, a storage unit 52, an interface (I/F) unit 54, a display unit driving unit 56, a display unit 58, an operation input detection unit 60, and an operation unit 62. The control unit 50, the storage unit 52, the I/F unit 54, the display unit driving unit 56, and the operation input detection unit 60 are connected to each other through a bus 63, such as a system bus or a control bus, such that they can transmit and receive various kinds of information.

The control unit 50 has a function of controlling the overall operation of the console 16. The control unit 50 comprises a central processing unit (CPU) 50A, a read only memory (ROM) 50B, and a random access memory (RAM) 50C. For example, various processing programs executed by the CPU 50A are stored in the ROM 50B in advance. The RAM 50C has a function of temporarily storing various kinds of data.

For example, the image data of the radiographic image captured by the mammography apparatus 12 is stored in the storage unit 52. Examples of the storage unit 52 include a hard disk drive (HDD) and a solid state drive (SSD).

The I/F unit 54 has a function of transmitting and receiving various kinds of information to and from the mammography apparatus 12 or an external system (for example, an RIS) using wireless communication or wired communication.

The display unit 58 has a function of displaying various kinds of information. The display unit driving unit 56 has a function of controlling the display of various kinds of information on the display unit 58.

The operation unit 62 is used by a user to input an instruction to capture a radiographic image or various kinds of information. The operation unit 62 is not particularly limited. Examples of the operation unit 62 include various switches, a touch panel, a touch pen, a plurality of keys, and a mouse. In a case in which the operation unit 62 is a touch panel, the operation unit 62 may be integrated with the display unit 58. The operation input detection unit 60 has a function of detecting the operation state of the operation unit 62.

The mammography apparatus 12 according to this embodiment comprises the radiation detector 22, the radiation source 24, the compression plate 28, the moving unit 30, the pressure sensors 25, the control unit 40, a storage unit 42, an I/F unit 44, and an operation panel 46. In addition, FIG. 4 illustrates only one pressure sensor 25. However, the mammography apparatus 12 according to this embodiment comprises n pressure sensors 25, as described above.

The radiation detector 22, the radiation source 24, the moving unit 30, the pressure sensors 25, the control unit 40, the storage unit 42, the I/F unit 44, and the operation panel 46 are connected to each other through a bus 49, such as a system bus or a control bus, such that they can transmit and receive various kinds of information.

The control unit 40 according to this embodiment is an example of a control unit according to the invention and has a function of controlling the overall operation of the mammography apparatus 12. In a case in which a radiographic image is captured, the control unit 40 also has a function of controlling the radiation detector 22, the radiation source 24, and the moving unit 30. The control unit 40 according to this embodiment comprises a CPU 40A, a ROM 40B, and a RAM 40C. For example, various processing programs including an imaging process program executed by the CPU 40A are stored in the ROM 40B in advance. The RAM 40C has a function of temporarily storing various kinds of data.

The storage unit 42 stores various kinds of information, such as a first compression pressure and a second compression pressure which are reference values, which will be described in detail below. Examples of the storage unit 42 include an HDD and an SSD.

The I/F unit 44 has a function of transmitting and receiving various kinds of information to and from the console 16, using wireless communication or wired communication.

The operation panel 46 is used by the user to check imaging conditions in the vicinity of the mammography apparatus 12 or to input instructions related to imaging. Therefore, the operation panel 46 has a function of displaying the imaging conditions or a function of receiving various input instructions. The operation panel 46 is provided as, for example, a liquid crystal panel and a plurality of switches or buttons in the mammography apparatus 12. In addition, the operation panel 46 may be provided as a touch panel display.

In this embodiment, various programs stored in the control unit 40 of the mammography apparatus 12 and the control unit 50 of the console 16 are stored in the ROMs of the control unit 40 and the control unit 50 in advance. However, the invention is not limited thereto. For example, various programs may be stored in a recording medium, such as a compact disk read only memory (CD-ROM) or a removable disk, and may be installed from the recording medium to the ROM. In addition, various programs may be installed from an external apparatus to, for example, the ROM through a communication line such as the Internet.

Next, the operation of the mammography apparatus 12 according to this embodiment will be described with reference to the drawings.

In the radiography system 10, in a case in which the image of the breast is captured, first, the user positions the breast of the subject on the imaging surface 27 of the imaging stand 26 of the mammography apparatus 12. The breast is compressed by the compression plate 28 between the imaging stand 26 and the compression plate 28 and is fixed.

In a case in which the mammography apparatus 12 captures a radiographic image of the breast, the breast compressed by the compression plate 28 is irradiated with the radiation R to capture a radiographic image. For example, the breast is compressed for the following reasons: the overlap between the mammary gland tissues is expanded and it is easy to determine whether the mammary gland tissue is a benign lesion or a malignant lesion; the blurring of a radiographic image is prevented and, for example, a mammary gland structure is visible; the breast is fixed and the movement of the body of the subject is prevented; and the thickness of the breast is reduced and the amount of exposure of the breast to radiation is reduced.

Figure 5:
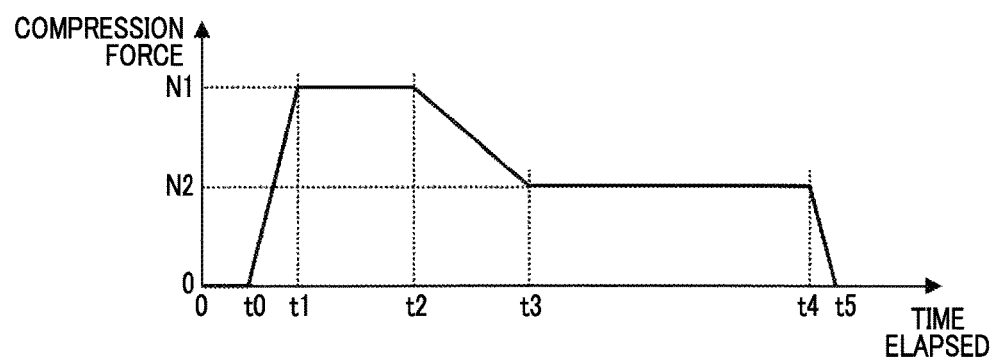
FIG. 5 is a timing chart illustrating an example of the relationship between a compression force and the time elapsed since the start of the compression of the breast.

However, when the breast is compressed by the compression plate 28, the breast is squeezed or stretched. Therefore, in many cases, the subject feels a pain. In the mammography apparatus according to the related art, a radiographic image is captured in a state in which the breast is compressed by a specific compression force (for example, a compression force that is generally used to capture the radiographic image of the breast). Therefore, while the breast is being compressed, the pain persists. In contrast, the inventors found that, for example, when a compression force to compress the breast was increased to a first compression force N1 (for example, the above-mentioned specific compression force) and was then reduced to a second compression force N2 less than the first compression force N1 as illustrated in FIG. 5, it was possible to effectively reduce the subject's pain caused by the compression of the breast. FIG. 5 is a timing chart illustrating an example of the relationship between the time elapsed since the start of the compression of the breast and the compression force applied to the breast. In the example illustrated in FIG. 5, the compression plate 28 comes into contact with the breast at a time t0. Then, the compression force is increased from 0 to the first compression force N1 for a period from the time t0 to a time t1. The compression of the breast by the first compression force N1 is maintained for a period from the time t1 to a time t2. The compression force is reduced from the first compression force N1 to the second compression force for a period from the time t2 to a time t3. The compression of the breast by the second compression force N2 is maintained for a period from the time t3 to a time t4. The compression force is reduced from the second compression force N2 to 0 for a period from the time t4 to a time t5.

Figure 6:
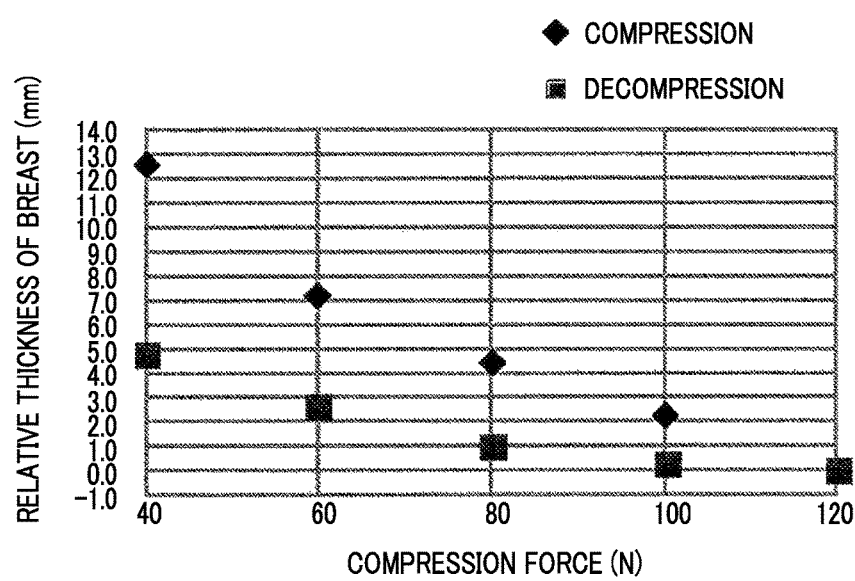
FIG. 6 is a graph illustrating an example of the relationship between the compression force in a case in which the breast is compressed according to the timing chart illustrated in FIG. 5 and the thickness of the breast with respect to the thickness of the breast in a case in which the compression force is 120 N.

In addition, the inventors found that, even when the breast was compressed by the first compression force N1 and then the compression force was reduced to the second compression force N2 lower than the first compression force N1, the thickness of the breast, specifically, the distance between the imaging surface 27 of the imaging stand 26 and a lower surface of the compression plate 28 was less likely to return to the original value. FIG. 6 illustrates an example of the relationship between the compression force in a case in which the breast is compressed according to the timing chart illustrated in FIG. 5 and the thickness of the breast with respect to the thickness (0) of the breast in a case in which the compression force is 120 N. In the example illustrated in FIG. 6, the first compression force N1 is 120 N and the second compression force N2 is 60 N. As illustrated in FIG. 6, even when the compression plate 28 is moved in the decompression direction to reduce the compression force, the thickness of the breast is less likely to return to the original value and a hysteresis relationship is established between the compression force and the thickness of the breast. Therefore, even when the compression force is reduced, for example, the expanded state of the overlap between the mammary gland tissues is maintained. That is, it is possible to satisfy the reason why the breast is compressed.

Figure 7:
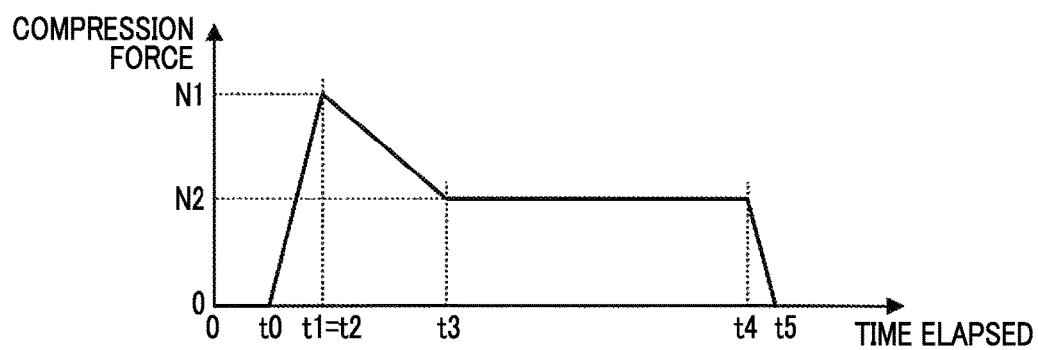
FIG. 7 is a timing chart illustrating an example of the relationship between the compression force and the time elapsed since the start of the compression of the breast in a case in which the time for which the breast is continuously compressed by a first compression force is 0.
Figure 8:
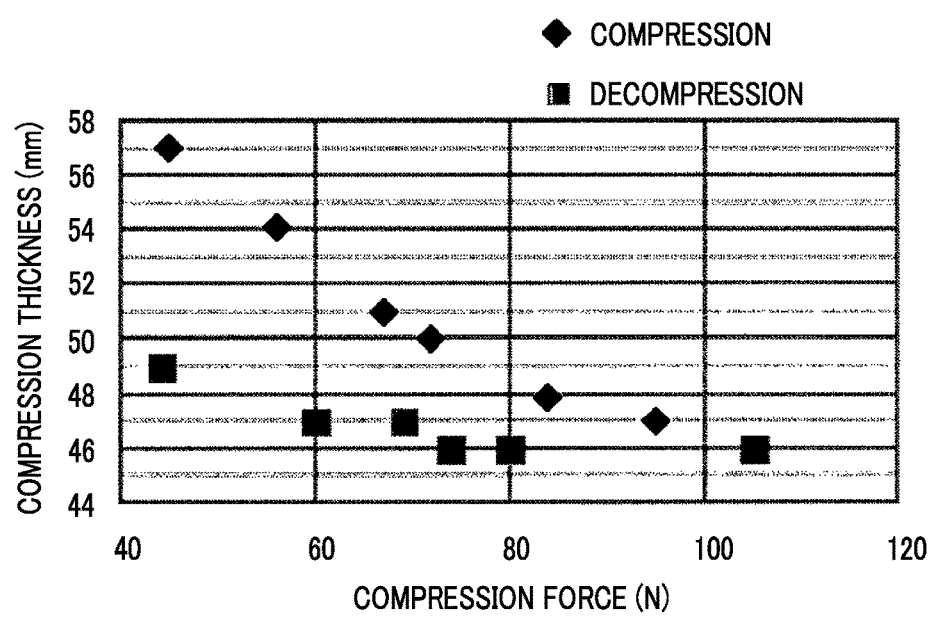
FIG. 8 is a graph illustrating an example of the relationship between the compression force in a case in which the breast is compressed according to the timing chart illustrated in FIG. 7 and the thickness of the breast with respect to the thickness of the breast in a case in which the compression force is 120 N.

Even if the time for which the breast is continuously compressed by the first compression force N1 (the time from the time t1 to the time t2) changes, the thickness of the breast is less likely to return to the original value although the compression force is reduced to the small second compression force N2 less than the first compression force N1 after the breast is compressed by the first compression force N1. FIG. 7 is a timing chart illustrating an example of the relationship between the compression force and the time elapsed since the start of the compression of the breast in a case in which the time for which the breast is continuously compressed by the first compression force N1 is 0. FIG. 8 illustrates an example of the relationship between the compression force in a case in which the breast is compressed according to the timing chart illustrated in FIG. 7 and the thickness of the breast compressed by the compression plate 28. In FIG. 8, the vertical axis directly indicates the thickness of the breast (compression thickness). As can be seen from the comparison between FIG. 6 and FIG. 8, in a case in which the breast is compressed by the first compression force N1 and the compression force is reduced to the second compression force N2, the thickness of the breast is less likely to return to the original value, regardless of the time for which the breast is continuously compressed by the first compression force N1. In this case, a hysteresis relationship is also established between the compression force and the thickness of the breast.

In a case in which the size of the breast is large, when the breast is compressed by the same compression force, the compression force is dispersed and the subject's pain tends to be less than that in a case in which the size of the breast is small. Therefore, it is preferable to finely control the movement of the compression plate 28 according to the size of the breast. For this reason, the mammography apparatus 12 according to this embodiment controls the compression of the breast by the compression plate 28 not on the basis of the compression force applied to the entire breast by the compression plate 28 but on the basis of a compression pressure which is a compression force per unit area.

In an imaging process performed by the mammography apparatus 12 according to this embodiment, after the breast is compressed by a first compression pressure, the compression pressure is reduced to a second compression pressure lower than the first compression pressure and the radiation R is emitted to capture a radiographic image in a state in which the second compression pressure is maintained. The first compression pressure and the second compression pressure will be described in detail below.

Figure 9:
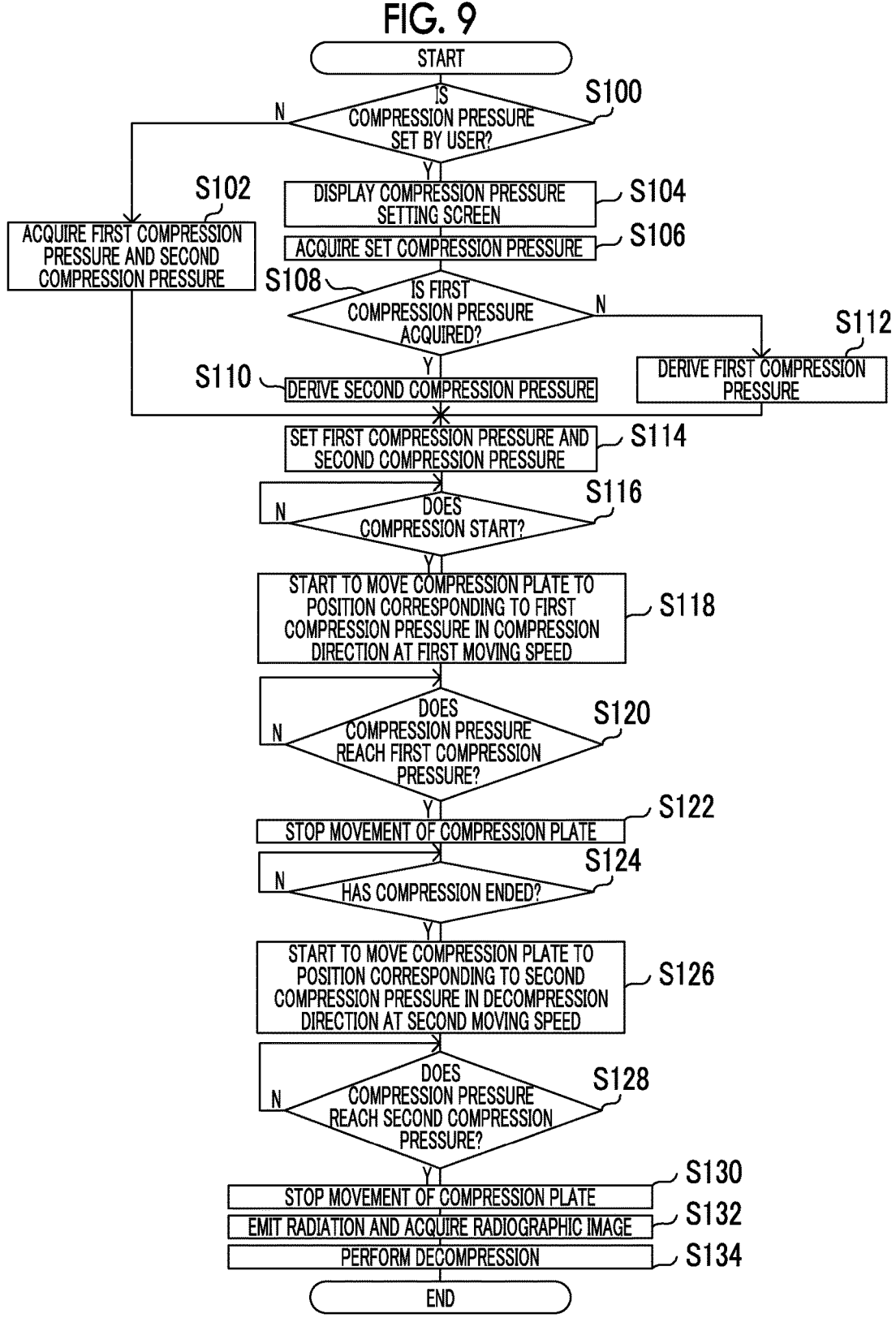
FIG. 9 is a flowchart illustrating an imaging process performed by a mammography apparatus according to the first embodiment.

When the user inputs an instruction to start to capture a radiographic image through the operation unit 62 of the console 16, the imaging start instruction and an imaging menu are transmitted to the mammography apparatus 12 through the I/F unit 54. In a case in which the instruction to start to capture a radiographic image is received from the console 16, the mammography apparatus 12 performs the imaging process. FIG. 9 is a flowchart illustrating an example of the flow of the imaging process performed by the control unit 40 of the mammography apparatus 12 according to this embodiment. In the mammography apparatus 12 according to this embodiment, the CPU 40A of the control unit 40 executes the imaging process program stored in the ROM 40B to perform the imaging process.

In Step S100, the control unit 40 determines whether a compression pressure is set by the user. In the mammography apparatus 12 according to this embodiment, the user can set the first compression pressure or the second compression pressure through the operation panel 46. In a case in which an instruction to set the compression pressure is not received from the operation panel 46 after a predetermined period of time (10 seconds in this embodiment) has elapsed, the determination result is "No" and the process proceeds to Step S102.

In Step S102, the control unit 40 acquires a predetermined first compression pressure and a predetermined second compression pressure and proceeds to Step S114. In this embodiment, the control unit 40 reads the first compression pressure and the second compression pressure, which are stored as reference values in the storage unit 42 in advance, from the storage unit 42 and acquires the first compression pressure and the second compression pressure. The control unit 40 can acquire the first compression pressure and the second compression pressure using any method. For example, in a case in which the first compression pressure and the second compression pressure are designated in the imaging menu, the first compression pressure and the second compression pressure may be acquired from the imaging menu.

On the other hand, in a case in which the instruction to set the compression pressure is received from the operation panel 46 in Step S100, the determination result is "Yes" and the process proceeds to Step S104.

Figure 10:
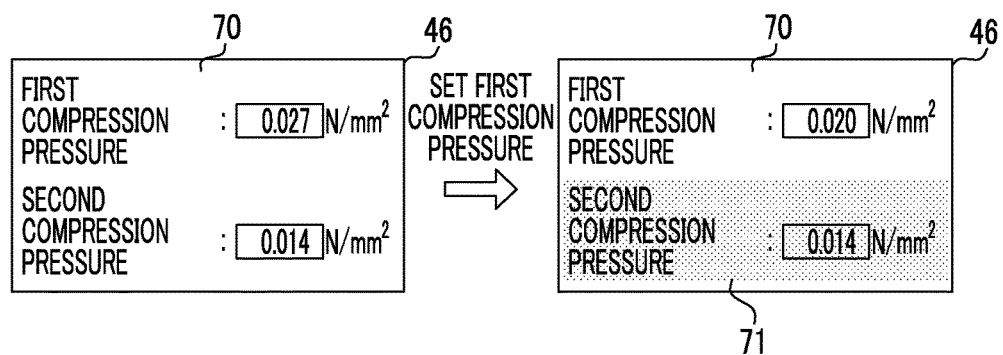
FIG. 10 is a diagram schematically illustrating an example of a compression pressure setting screen.

In Step S104, the control unit 40 displays a compression pressure setting screen 70 which is illustrated in FIG. 10 on the operation panel 46. A reference value of the first compression pressure and a reference value of the second compression pressure are displayed on the compression pressure setting screen 70 illustrated in FIG. 10 in advance for reference. In this embodiment, the reference value of the first compression pressure is a 0.027 N/mm$^2$ that is obtained by converting a compression force of 60 N, which is used to compresses the breast in a general mammography apparatus, into a compression pressure which a compression force per unit area. The reference value of the second compression pressure is 0.014 N/mm$^2$ that is half (about half since the reference value is rounded off) the reference value of the first compression pressure in order to reduce the subject's pain and to prevent the deviation of the breast due to the movement of the body of the subject. The user sets the first compression pressure or the second compression pressure, using buttons included in the operation panel 46. FIG. 10 illustrates an example in which the user sets the first compression pressure from 0.027 N/mm$^2$ to 0.020 N/mm$^2$. In the mammography apparatus 12 according to this embodiment, the user may set only one of the first compression pressure and the second compression pressure. In a case in which the user sets one of the first compression pressure and the second compression pressure, the control unit 40 prohibits the setting of the other compression pressure and displays information 71 indicating that the setting of the other compression pressure has been prohibited on the compression pressure setting screen 70. In the example illustrated in FIG. 10, a state in which a portion for setting the second compression pressure is displayed in dark is illustrated as the information 71 indicating that the setting has been prohibited.

Then, in Step S106, the control unit 40 acquires the first compression pressure or the second compression pressure set by the user through the operation panel 46.

Then, in Step S108, the control unit 40 determines whether the first compression pressure has been acquired. In a case in which the first compression pressure has been acquired, the determination result is "Yes" and the process proceeds to Step S110.

In Step S110, the control unit 40 derives the second compression pressure on the basis of the acquired first compression pressure and proceeds to Step S114.

Here, the first compression pressure and the second compression pressure according to this embodiment will be described. The first compression pressure is preferably in the range of 0.018 N/mm$^2$ to 0.045 N/mm$^2$ in order to expand the mammary gland tissues and to reduce the subject's pain and the reference value of the first compression pressure is more preferably 0.027 N/mm$^2$. In addition, the second compression pressure is lower than the first compression pressure and is preferably in the range of 0.009 N/mm$^2$ to 0.023 N/mm$^2$ in order to effectively reduce the subject's pain and to prevent the movement of the body of the subject and the reference value of the second compression pressure is more preferably 0.014 N/mm$^2$.

The examination result of the inventors proves that the second compression pressure is preferably in the range of 40% to 70% of the first compression pressure and is more preferably 50% of the first compression pressure. Alternatively, the second compression pressure is preferably 0.007 N/mm$^2$ to 0.021 N/mm$^2$ less than the first compression pressure and is more preferably 0.013 N/mm$^2$ less than the first compression pressure.

In other words, the first compression pressure is preferably in the range of 143% to 250% of the second compression pressure and is more preferably 200% of the second compression pressure. Alternatively, the first compression pressure is preferably 0.007 N/mm$^2$ to 0.021 N/mm$^2$ greater than the second compression pressure and is more preferably 0.013 N/mm$^2$ greater than the second compression pressure.

In the mammography apparatus 12 according to this embodiment, information indicating the correspondence relationship between the first compression pressure and the second compression pressure in the above-mentioned ranges is stored in the storage unit 42 in advance and the first compression pressure or the second compression pressure which has not been set by the user is derived on the basis of the information.

Therefore, in this step, the control unit 40 derives the second compression pressure on the basis of the first compression pressure and the information indicating the correspondence relationship between the first compression pressure and the second compression pressure.

On the other hand, in a case in which the second compression pressure is acquired in Step S106, the determination result in Step S108 is "No" and the process proceeds to Step S112. In Step S112, the control unit 40 derives the first compression pressure on the basis of the second compression pressure and the information indicating the correspondence relationship between the first compression pressure and the second compression pressure and proceeds to Step S114.

In Step S114, the control unit 40 sets the first compression pressure and the second compression pressure obtained by the above-mentioned process as target values in the moving unit 30.

Then, in Step S116, the control unit 40 determines whether to start the compression of the breast by the compression plate 28. When the positioning of the breast ends, the user inputs a compression start instruction through the operation panel 46 in order to start the compression of the breast. In Step S116, the control unit 40 determines not to start the compression until the compression start instruction is input and is in a standby state. On the other hand, when the compression start instruction is input, the control unit 40 determines to start the compression and proceeds to Step S118.

In Step S118, the control unit 40 directs the moving unit 30 to start to move the compression plate 28 in the compression direction. Specifically, the control unit 40 starts to move the compression plate 28 from an initial position in the compression direction at a first predetermined moving speed. The control unit 40 moves the compression plate 28 in the compression direction to compress the breast. In the mammography apparatus 12 according to this embodiment, the position where the compression plate 28 does not compress the breast is predetermined as the initial position.

Figure 11:
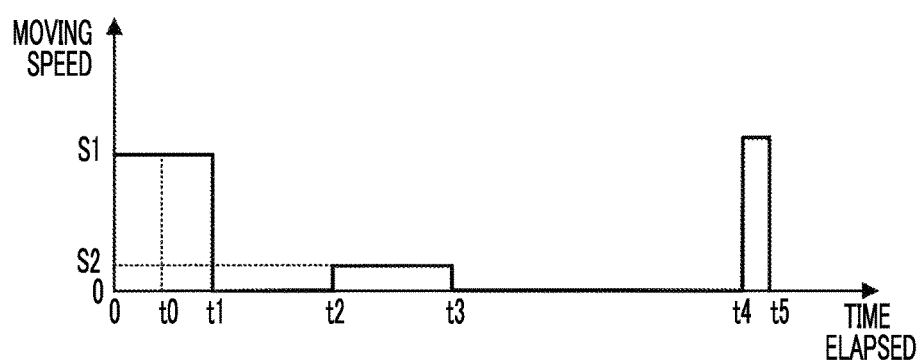
FIG. 11 is a timing chart illustrating an example of the correspondence relationship between a compression pressure applied to the breast and the time elapsed in a case in which the compression plate is moved according to the timing chart illustrated in FIG. 5.

In general, the moving speed of the compression plate 28 is preferably in the range of 0.5 mm/s to 50 mm/s, for example, in order to prevent the movement of the body of the subject due to the movement of the compression plate 28 or to reduce an imaging time (the time for which the breast is compressed by the compression plate 28). In this embodiment, for the moving speed of the compression plate 28, a first moving speed at which the compression plate 28 is moved from the initial position to a position corresponding to the first compression pressure is higher than a second moving speed at which the compression plate 28 is moved from the position corresponding to the first compression pressure to a position corresponding to the second compression pressure for the following reason. FIG. 11 is a timing chart illustrating an example of the correspondence relationship between the compression pressure applied to the breast and the time elapsed in a case in which the compression plate 28 is moved according to the timing chart illustrated in FIG. 5. In the example illustrated in FIG. 11, a moving speed S1 corresponds to the first moving speed and a moving speed S2 corresponds to the second moving speed.

A movement distance from the initial position to the position corresponding to the first compression pressure is relatively long. Therefore, when the moving speed of the compression plate 28 is low, the time for which the subject feels a pain increases and a burden on the subject increases. In addition, the total time required for imaging increases and the efficiency of imaging is reduced. For this reason, the first moving speed is set to a high value. In the mammography apparatus 12 according to this embodiment, the first moving speed is preferably in the range of 1 mm/s to 50 mm/s which is the above-mentioned general moving speed range and is more preferably 10 mm/s.

The distance from the position corresponding to the first compression pressure to the position corresponding to the second compression pressure is shorter than the movement distance of the compression plate 28 at the first moving speed. When the compression plate 28 is moved at an excessively high speed, there is a concern that the compression pressure will deviate from the second compression pressure which is a target compression pressure. Therefore, the second moving speed is lower than the first moving speed, for example, in order to prevent the deviation of the compression pressure from the second compression pressure. In the mammography apparatus 12 according to this embodiment, the second moving speed is preferably in the range of 0.5 mm/s to 20 mm/s which is the above-mentioned general moving speed range and is more preferably 1 mm/s.

In this embodiment, the control unit 40 repeatedly acquires the detection results of the pressure sensors 25 at a predetermined interval (0.1 seconds in this embodiment) and moves the compression plate 28 in the compression direction to compress the breast, using the moving unit 30, until the compression pressure derived on the basis of the detection results of the pressure sensors 25 reaches the first compression pressure.

Then, in Step S120, the control unit 40 derives the compression pressure on the basis of the detection results acquired from each pressure sensor 25. A method for deriving the compression pressure is not particularly limited. For example, the control unit 40 may select the maximum value from the detection results of the n pressure sensors 25 and may derive the compression pressure on the basis of the selected maximum value and the pressure detection area. In addition, for example, the control unit 40 may select a predetermined number of detection results in descending order from the detection results of the n pressure sensors 25 and may derive the compression pressure on the basis of the average value of the selected detection results and the pressure detection area. For example, the detection result of the pressure sensor 25 provided in a portion of the imaging surface 27 with which the breast does not come into contact little changes from 0 N/mm$^2$. Therefore, the control unit 40 may derive the compression pressure on the basis of the average value of other detection results except 0 N/mm$^2$ or the detection results in a predetermined range from 0 N/mm$^2$, considering errors, and a pressure detection area. As such, it is preferable to derive the compression pressure, using the detection results of the pressure sensors 25 provided in a portion of the imaging surface 27 with which the breast comes into contact.

The control unit 40 compares the derived compression pressure with the first compression pressure set in the moving unit 30 and determines whether the compression pressure reaches the first compression pressure. In a case in which the compression pressure does not reach the first compression pressure, the determination result is "No" and the control unit 40 is in the standby state. On the other hand, in a case in which the compression pressure reaches the first compression pressure, the determination result is "Yes" and the process proceeds to Step S122.

In Step S122, the control unit 40 stops the movement of the compression plate 28 by the moving unit 30.

Then, in Step S124, the control unit 40 determines whether to end the continuous compression with the first compression pressure. The duration for which the compression of the breast by the first compression pressure is maintained is not particularly limited and is preferably equal to or more than 0.5 seconds. The examination result of the invention proves that the duration is preferably less than 8 seconds or the time from the start of compression with the first compression pressure to the end of compression with the second compression pressure is preferably less than 8 seconds, considering the return of the thickness of the breast to the original value. In addition, the user may determine the duration, considering the time for which the compression conditions of the breast of the subject are finely adjusted. The duration may be predetermined in, for example, the mammography apparatus 12 or may be set by the user through the operation panel 46. Furthermore, the control unit 40 may derive the duration according to the type of breast which will be described in detail below.

In Step S124, while the compression with the first compression pressure is maintained, the determination result is "No". On the other hand, in Step S124, when the time for which the compression with the first compression pressure is maintained elapses, the determination result is "Yes" and the process proceeds to Step S126.

In Step S126, the control unit 40 directs the moving unit 30 to start to move the compression plate 28 in the decompression direction at the second moving speed. The control unit 40 moves the compression plate 28 in the decompression direction to reduce the compression force applied to the breast.

In this embodiment, the control unit 40 repeatedly acquires the detection results of the pressure sensors 25 at a predetermined interval (0.1 seconds in this embodiment) and moves the compression plate 28 in the decompression direction to reduce the compression pressure applies to the breast, using the moving unit 30, until the compression pressure derived on the basis of the detection results of the pressure sensors 25 reaches the second compression pressure.

Then, in Step S128, the control unit 40 compares the compression pressure derived on the basis of the detection results of the pressure sensors 25 with the second compression pressure set in the moving unit 30 and determines whether the compression pressure reaches the second compression pressure. In a case in which the compression pressure does not reach the second compression pressure, the determination result is "No" and the control unit 40 is in the standby state. On the other hand, in a case in which the compression pressure reaches the second compression pressure, the determination result is "Yes" and the process proceeds to Step S130.

In Step S130, the control unit 40 stops the movement of the compression plate 28 by the moving unit 30. When the movement of the compression plate 28 is stopped, the user inputs an instruction to start the emission of the radiation R. It is preferable that the instruction to start the emission of the radiation R is input by a dedicated irradiation switch (not illustrated). The instruction may be input through, for example, the operation unit 62 of the console 16. The instruction may be input in any way according to the structure of the mammography apparatus.

Then, in Step S132, the control unit 40 directs the radiation source 24 to emit the radiation R to the breast of the subject at the time corresponding to the irradiation start instruction from the user and the radiation detector 22 captures a radiographic image.

Then, in Step S134, the control unit 40 moves the compression plate 28 to the initial position in the decompression direction to decompress the breast, using the moving unit 30, and ends the imaging process. The moving speed in a case in which the compression plate 28 is moved in the decompression direction after the radiographic image is acquired is not particularly limited. It is preferable that the moving speed is as high as possible in order to rapidly remove the subject's pain.

Second Embodiment

In the first embodiment, the case in which the second compression pressure is the reference value or the compression pressure set by the user has been described. However, in general, a reaction force to compression or the subject's pain varies depending on the type of breast, for example, the thickness, cup size (hereinafter, simply referred to as a "cup"), size, weight, and hardness of the breast and mammary gland density. Therefore, in the second (this embodiment) to seventh embodiments, a case in which the breast is compressed by the second compression pressure corresponding to the type of breast will be described.

First, in this embodiment, a case in which the breast is compressed by the second compression pressure corresponding to the thickness of the breast as the type of breast will be described.

Figure 12:
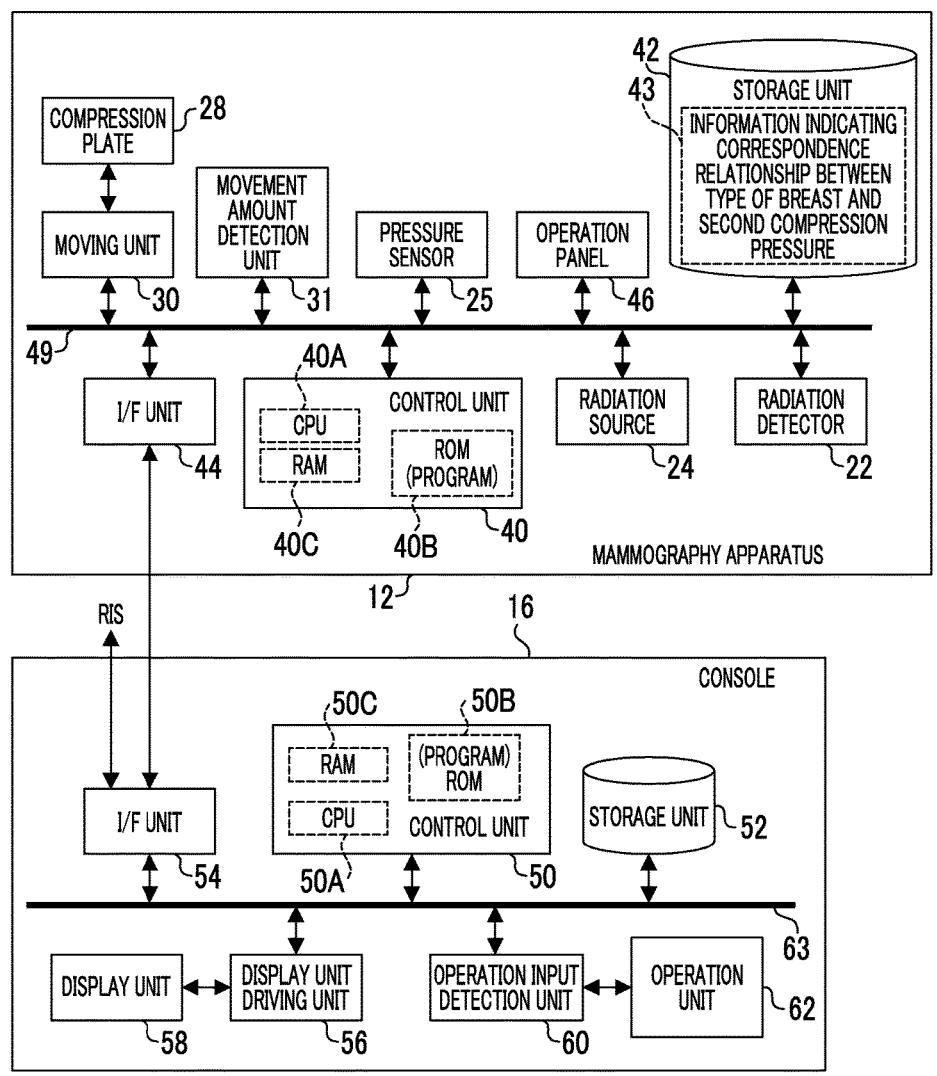
FIG. 12 is a block diagram illustrating the structure of a radiography system according to a second embodiment.

As illustrated in FIG. 12, a mammography apparatus 12 according to this embodiment differs from the mammography apparatus 12 (see FIG. 4) according to the first embodiment in that it comprises a movement amount detection unit 31.

The movement amount detection unit 31 has a function of detecting the amount of movement (movement distance) in a case in which the compression plate 28 is moved in the compression direction or the decompression direction. A method for detecting the amount of movement of the compression plate 28 is not particularly limited. For example, a correspondence relationship between the number of revolutions of a rotating shaft of the motor 38 and the amount of movement of the compression plate 28 may be obtained in advance and the amount of movement of the compression plate 28 may be detected on the basis of the correspondence relationship and the number of revolutions of the rotating shaft of the motor 38 rotated in order to move the compression plate 28.

As illustrated in FIG. 12, the mammography apparatus 12 according to this embodiment differs from the mammography apparatus 12 (see FIG. 4) according to the first embodiment in that information 43 indicating a correspondence relationship between the type of breast and the second compression pressure is stored in the storage unit 42 in advance.

In general, the thickness of the breast is associated with the size of the breast. As the thickness of the breast increases, the size of the breast increases. The "thickness" of the breast means the thickness of the breast in a state in which the breast is compressed by a predetermined compression pressure (the first compression pressure in this embodiment).

As the size of the breast increases, a reaction force from the breast to the compression plate 28 increases and the breast is less likely to be squeezed. Therefore, as the thickness of the breast increases, the mammography apparatus 12 according to this embodiment increases the second compression pressure to appropriately compress the breast.

In the mammography apparatus 12 according to this embodiment, any one of information items 43A1 to 43A3 indicating the correspondence relationship between the thickness of the breast and the second compression pressure, which are illustrated in FIGS. 13A to 13C, respectively, is used as the information 43 indicating the correspondence relationship between the type of breast and the second compression pressure. As illustrated in FIGS. 13A to 13C, a plurality of second compression pressures associated with the thickness of the breast correspond to second compression pressure candidates according to the invention.

In the information 43A1 indicating the correspondence relationship between the thickness of the breast and the second compression pressure which is illustrated in FIG. 13A, the correspondence relationship between the thickness of the breast and the second compression pressure is shown. In the example illustrated in FIG. 13A, in a case in which the thickness of the breast is a "large" value greater than a normal value, the second compression pressure is 0.016 N/mm$^2$. In a case in which the thickness of the breast is the "normal" value, the second compression pressure is 0.014 N/mm$^2$. In a case in which the thickness of the breast is a "small" value less than the normal value, the second compression pressure is 0.012 N/mm$^2$. For example, in a case in which the thickness of the breast is the "normal" value, specifically, the thickness may be the average value of the thicknesses of a plurality of breasts which are obtained by experiments in advance or may be set by the user.

In the information 43A2 indicating the correspondence relationship between the thickness of the breast and the second compression pressure which is illustrated in FIG. 13B, the correspondence relationship between the thickness of the breast and the difference between the second compression pressure and a reference value is shown. In the example illustrated in FIG. 13B, in a case in which the thickness of the breast is a "normal" value, the difference between the second compression pressure and the reference value that is stored in the storage unit 42 in advance is 0, that is, the second compression pressure is a reference value. In a case in which the thickness of the breast is a "large" value greater than the normal value, the second compression pressure is a compression pressure obtained by adding 0.002 N/mm$^2$ to the reference value. In a case in which the thickness of the breast is a "small" value less than the normal value, the second compression pressure is a compression pressure obtained by subtracting 0.002 N/mm² from the reference value.

In the information 43A3 indicating the correspondence relationship between the thickness of the breast and the second compression pressure which is illustrated in FIG. 13C, the correspondence relationship between the thickness of the breast and the percentage of the second compression pressure with respect to the reference value is shown. In the example illustrated in FIG. 13C, in a case in which the thickness of the breast is a "normal" value, the second compression pressure is 100% of the reference value that is stored in the storage unit 42 in advance, that is, the second compression pressure is a reference value. In a case in which the thickness of the breast is a "large" value greater than the normal value, the second compression pressure is 115% of the reference value. In a case in which the thickness of the breast is a "small" value less than the normal value, the second compression pressure is 85% of the reference value.

In addition, it goes without saying that the information indicating the correspondence relationship between the thickness of the breast and the second compression pressure is not limited to that illustrated in FIGS. 13A to 13C. For example, in the examples illustrated in FIGS. 13A to 13C, the thickness of the breast is classified into three stages. However, the invention is not limited thereto. The thickness of the breast may be classified into two stages or four or more stages.

Figure 14:
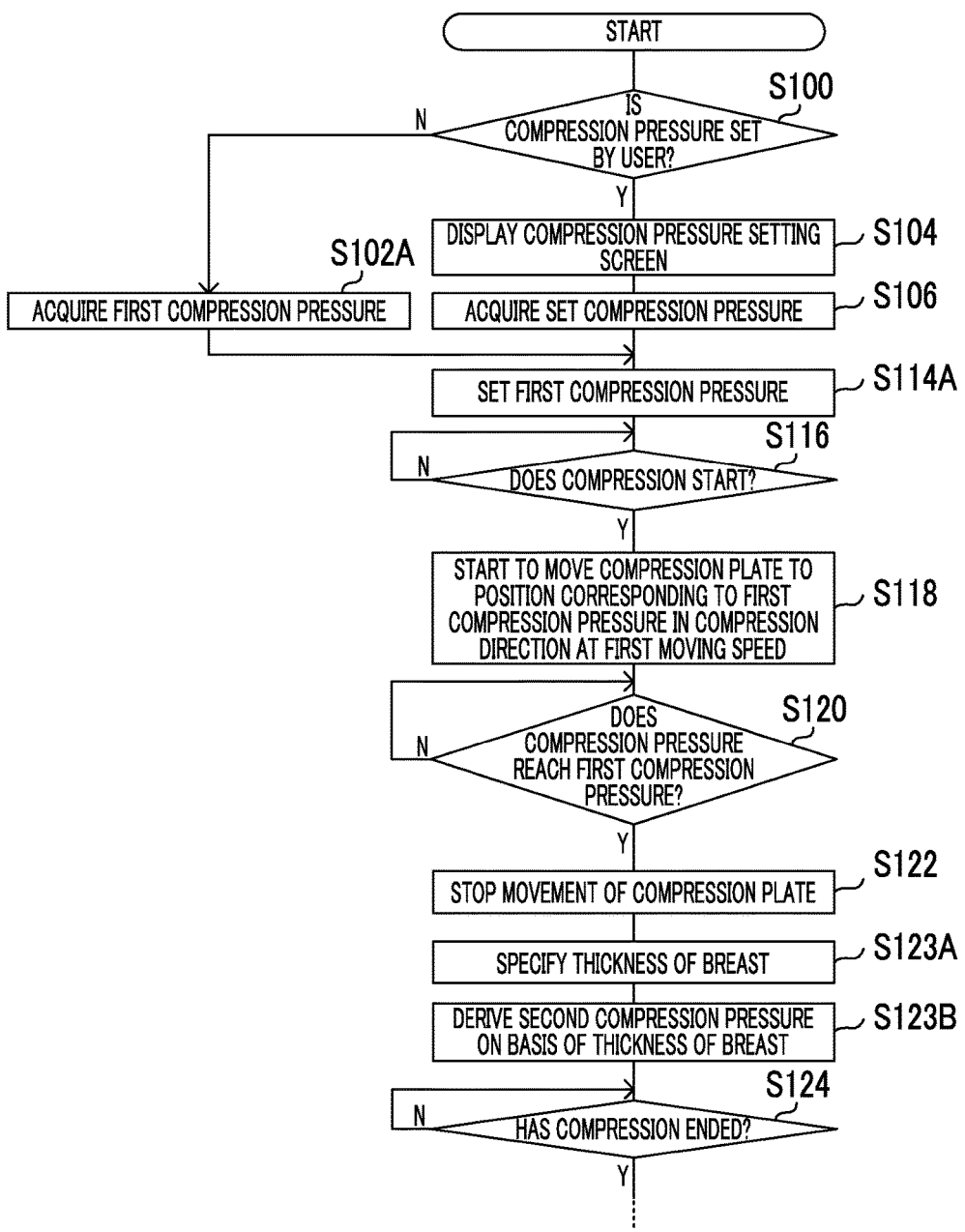
FIG. 14 is a flowchart illustrating an imaging process performed by a mammography apparatus according to the second embodiment.

As such, in the mammography apparatus 12 according to this embodiment, as described above, the second compression pressure corresponds to the thickness of the breast. Therefore, as illustrated in FIG. 14, an imaging process performed by the control unit 40 of the mammography apparatus 12 according to this embodiment differs from the imaging process (see FIG. 9) performed by the control unit 40 of the mammography apparatus 12 according to the first embodiment in a process related to the acquisition (derivation) of the second compression pressure.

That is, the imaging process performed by the control unit 40 according to this embodiment differs from the imaging process according to the first embodiment in that it includes Step S102A instead of Step S102 according to the first embodiment and includes Step S114A instead of Step S114.

In the mammography apparatus 12 according to this embodiment, since the control unit 40 derives the second compression pressure according to the type of breast, the user can set only the first compression pressure. Therefore, the imaging process performed by the control unit 40 according to this embodiment differs from the imaging process according to the first embodiment in that it does not include Steps S108 to S112 according to the first embodiment.

In Step S102A, the control unit 40 acquires only the first compression pressure.

In the imaging process according to this embodiment, in Step S106, the control unit 40 acquires the first compression pressure as the compression pressure set by the user. After the first compression pressure is acquired, the process proceeds to Step S114A. In Step S114A, the control unit 40 sets the first compression pressure as a target value in the moving unit 30.

In addition, the imaging process performed by the control unit 40 according to this embodiment differs from the imaging process (see FIG. 9) according to the first embodiment in that it includes Step S123A and Step S123B between Step S122 and Step S124.

In Step S123A, the control unit 40 specifies the thickness of the breast of the subject on the basis of the detection result of the movement amount detection unit 31. Here, the control unit 40 acquires the amount of movement of the compression plate 28 from the initial position to the position corresponding to the first compression pressure as the detection result of the movement amount detection unit 31. In this embodiment, a gap (hereinafter, referred to as an "initial gap") between the initial position and the imaging surface 27 is obtained in advance and the acquired amount of movement is subtracted from the initial gap to calculate the thickness of the breast. The control unit 40 specifies the thickness of the breast on the basis of which of the classifications of the "large", "normal", and "small" values the calculated thickness corresponds to. In this way, the thickness of the breast in a case in which the breast is compressed by the first compression pressure is specified.

Then, in Step S123B, the control unit 40 derives the second compression pressure on the basis of the specified thickness of the breast and information 43A indicating the correspondence relationship between the thickness of the breast and the second compression pressure.

It goes without saying that a method for specifying the thickness of the breast is not limited to the above-mentioned method. For example, the thickness of the breast may be specified by the position of the compression plate 28 detected by a potentiometer. For example, the thickness of the breast may be specified by the image of the side of the compressed breast which is captured by an optical camera. In addition, for example, the gap between the compression plate 28 and the imaging surface 27 may be detected by sensors, such as infrared sensors provided at four corners of the compression plate 28, and the thickness of the breast may be specified on the basis of the detected gap.

Third Embodiment

In this embodiment, a case in which the breast is compressed by the second compression pressure corresponding to the cup of the breast as the type of breast will be described.

Figure 15:
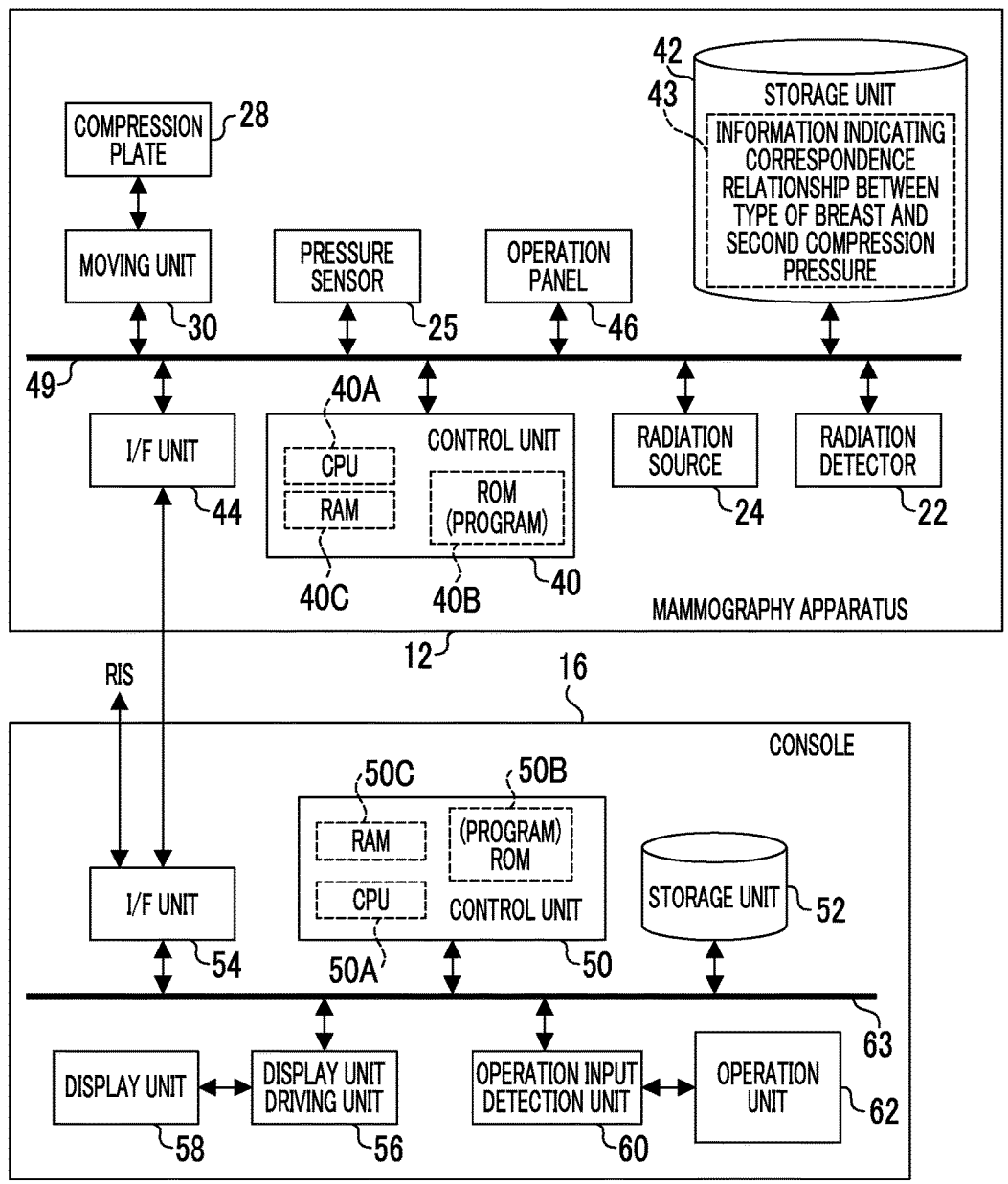
FIG. 15 is a block diagram illustrating the structure of a radiography system according to a third embodiment.

As illustrated in FIG. 15, a mammography apparatus 12 according to this embodiment differs from the mammography apparatus 12 (see FIG. 4) according to the first embodiment in that the information 43 indicating the correspondence relationship between the type of breast and the second compression pressure is stored in the storage unit 42 in advance, as in the mammography apparatus 12 according to the second embodiment.

In general, the cup of the breast is associated with the size of the breast. As the cup of the breast increases, the size of the breast increases. In Japan, the cup of the breast means the difference between the top bust and the under bust.

As described above, as the size of the breast increases, a reaction force from the breast to the compression plate 28 increases and the breast is less likely to be squeezed. Therefore, as the cup of the breast increases, the mammography apparatus 12 according to this embodiment increases the second compression pressure to appropriately compress the breast.

In the mammography apparatus 12 according to this embodiment, in information 43B indicating the correspondence relationship between the cup of the breast and the second compression pressure illustrated in FIG. 16 which is used as the information 43 indicating the correspondence relationship between the type of breast and the second compression pressure, the correspondence relationship between the cup of the breast and the second compression pressure is shown. In the example illustrated in FIG. 16, in a case in which the cup of the breast is "A or B", that is, in a case in which the cup is relatively small, the second compression pressure is 0.012 N/mm$^2$. In a case in which the cup of the breast is "C or D", the second compression pressure is 0.014 N/mm$^2$. In a case in which the cup of the breast is "equal to or greater than E", that is, in a case in which the cup is relatively large, the second compression pressure is 0.016 N/mm$^2$.

It goes without saying that the information 43B indicating the correspondence relationship between the cup of the breast and the second compression pressure is not limited to that illustrated in FIG. 16. For example, as described in the second embodiment with reference to FIG. 13B, information indicating the correspondence relationship between the cup of the breast and the difference between the second compression pressure and the reference value may be used. As described with reference to FIG. 13C, information indicating the correspondence relationship between the cup of the breast and the percentage of the second compression pressure with respect to the reference value may be used. For example, the cup of the breast may be classified into two stages or four or more stages.

Figure 17:
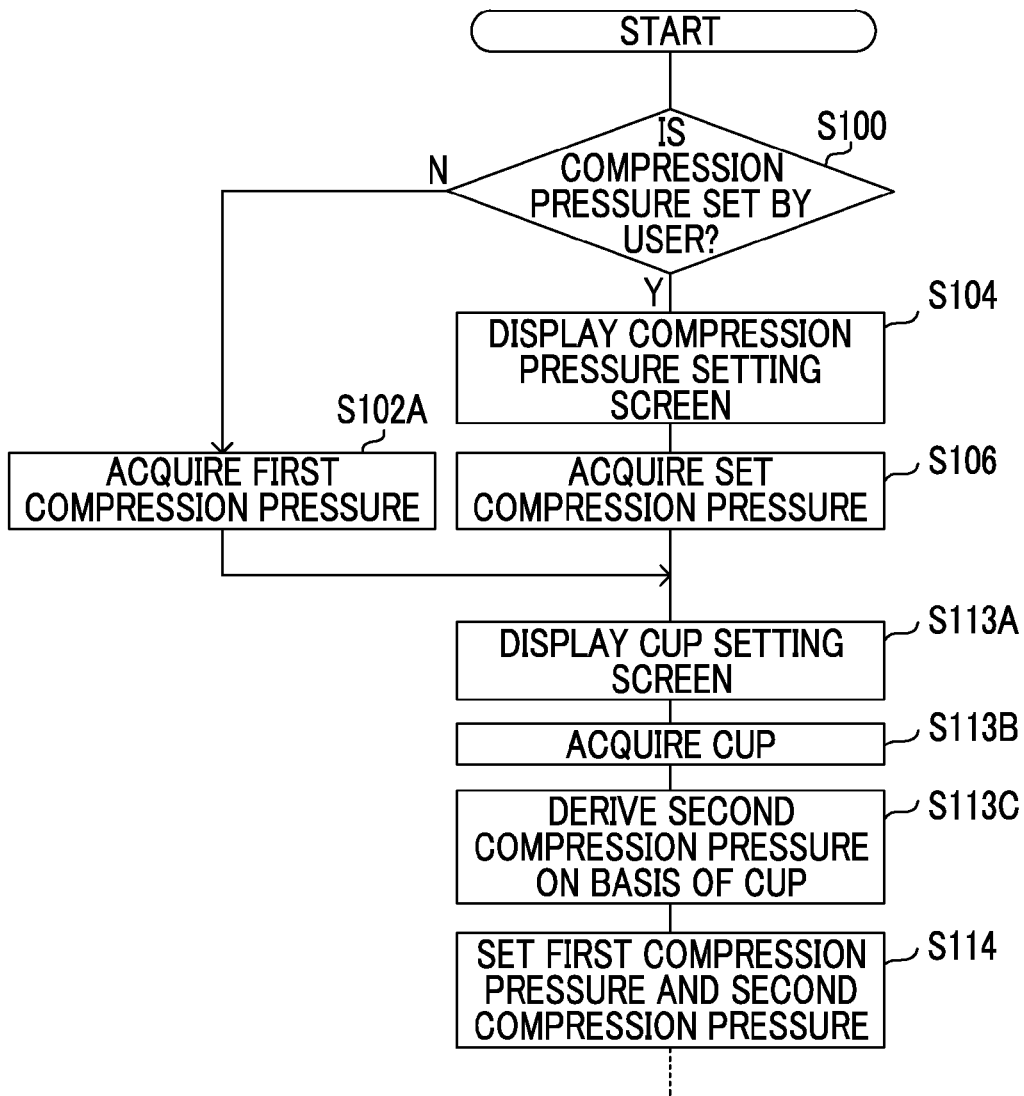
FIG. 17 is a flowchart illustrating an imaging process performed by a mammography apparatus according to the third embodiment.

In the mammography apparatus 12 according to this embodiment, as described above, the second compression pressure corresponds to the cup of the breast. Therefore, as illustrated in FIG. 17, an imaging process performed by the control unit 40 of the mammography apparatus 12 according to this embodiment differs from the imaging process (see FIG. 9) performed by the control unit 40 of the mammography apparatus 12 according to the first embodiment in a process related to the acquisition (derivation) of the second compression pressure.

That is, the imaging process performed by the control unit 40 according to this embodiment differs from the imaging process (see FIG. 9) according to the first embodiment in that it includes Step S102A instead of Step S102 according to the first embodiment, includes Steps S113A to S113C before Step S114, and does not include Steps S108 to S112.

In Step S102A, the control unit 40 acquires only the first compression pressure, as in the imaging process according to the second embodiment.

Figure 18:
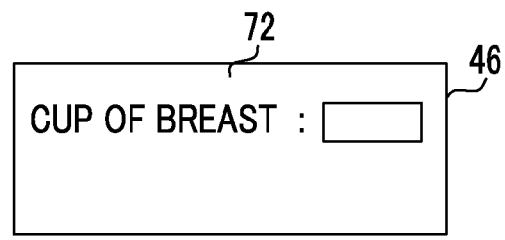
FIG. 18 is a diagram schematically illustrating an example of a cup setting screen.

In Step S113A, the control unit 40 displays a cup setting screen 72 illustrated in FIG. 18 on the operation panel 46. The user sets the cup of the breast, using the buttons included in the operation panel 46.

Then, in Step S113B, the control unit 40 acquires the cup of the breast set by the user through the operation panel 46.

Then, in Step S113C, the control unit 40 derives the second compression pressure on the basis of the cup of the breast and the information 43B indicating the correspondence relationship between the cup of the breast and the second compression pressure.

In this embodiment, the case in which the mammography apparatus 12 acquires the cup of the breast set by the user through the operation panel 46 has been described. However, a method for acquiring the cup of the breast is not limited thereto. For example, in a case in which information about the cup of the breast is included in the imaging menu, the cup of the breast may be acquired from the imaging menu.

For example, the control unit 40 of the mammography apparatus 12 may derive the cup of the breast. For example, as described above, in a case in which the cup of the breast is the difference between the top bust and the under bust, there is a correspondence relationship between the cup of the breast and the distance from the chest wall to the nipple of the subject in a state in which the breast is positioned on the imaging stand 26. Therefore, the correspondence relationship between the cup of the breast and the distance from the chest wall to the nipple of the subject may be obtained in advance by experiments. The distance from the chest wall to the nipple of the subject on the imaging stand 26 may be detected. The control unit 40 may derive the cup of the breast on the basis of the detected distance and the correspondence relationship. Here, a method for detecting the distance from the chest wall to the nipple of the subject on the imaging stand 26 is not particularly limited. For example, the control unit 40 may acquire a pre-image, perform image analysis for the acquired pre-image to detect the position of the nipple, and detect the distance from the chest wall to the nipple of the subject on the basis of the detected position of the nipple, as in a fourth embodiment which will be described below.

Fourth Embodiment

In this embodiment, a case in which the breast is compressed by the second compression pressure corresponding to the size of the breast as the type of breast will be described. In this embodiment, a case in which the control unit 40 specifies the size of the breast from a captured radiographic image of the breast will be described.

Figure 19:
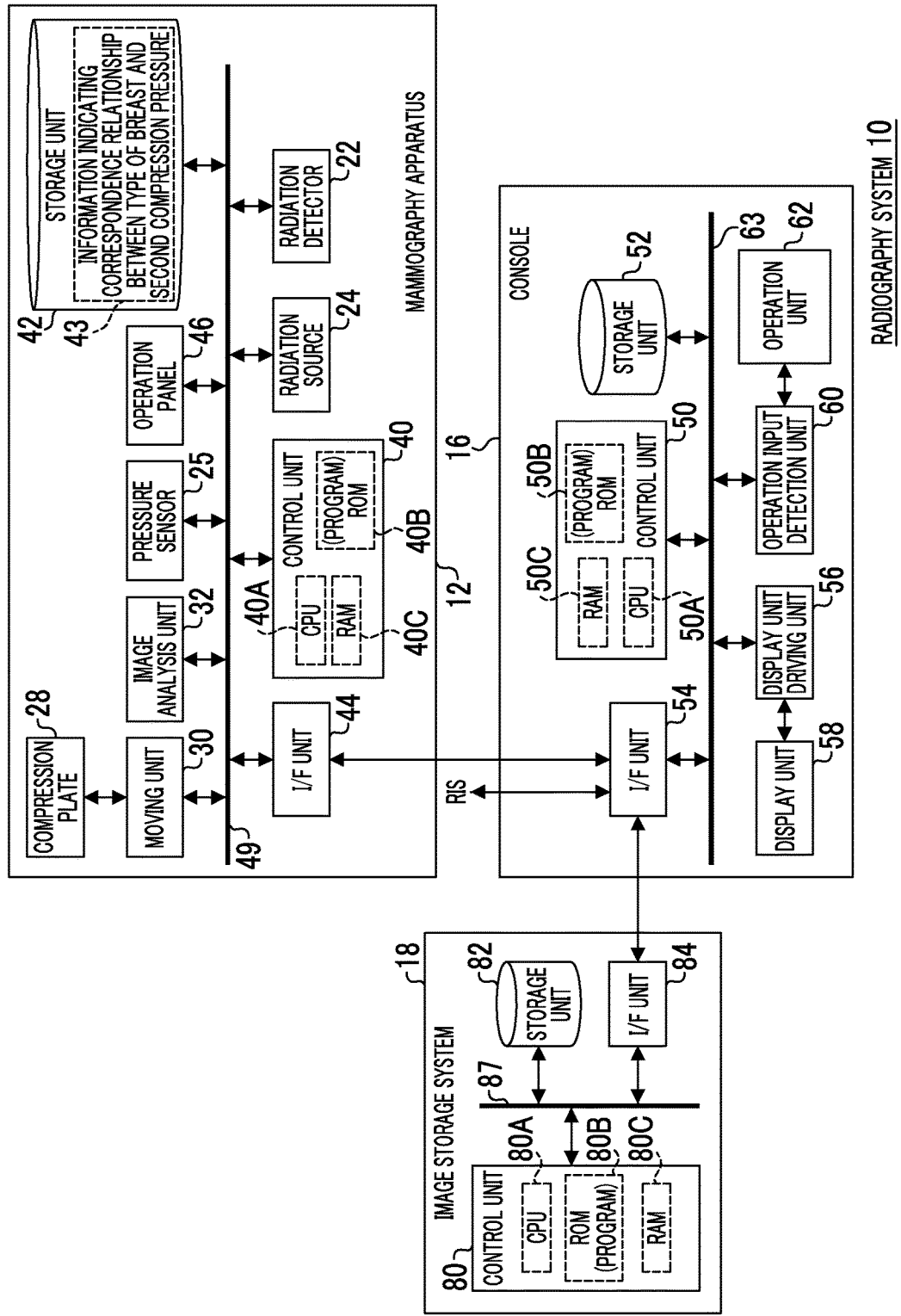
FIG. 19 is a block diagram illustrating the structure of a radiography system according to a fourth embodiment.

As illustrated in FIG. 19, a radiography system 10 according to this embodiment differs from the radiography system 10 (see FIG. 4) according to the first embodiment in that it comprises an image storage system 18.

The image storage system 18 has a function of storing the radiographic images captured by the mammography apparatus 12 in response to an instruction from the console 16 and a function of reading a radiographic image corresponding to a request from the console 16 and transmitting the radiographic image to the console 16. An example of the image storage system 18 is a picture archiving and communication system (PACS).

The image storage system 18 comprises a control unit 80, a storage unit 82, and an I/F unit 84. The control unit 80, the storage unit 82, and the I/F unit 84 are connected to each other by a bus 87, such as a system bus or a control bus, such that they can transmit and receive various kinds of information.

The control unit 80 has a function of controlling the overall operation of the image storage system 18. The control unit 80 comprises a CPU 80A, a ROM 80B, and a RAM 80C. Various processing programs executed by the CPU 80A are stored in the ROM 80B in advance. The RAM 80C has a function of temporarily storing various kinds of data.

The storage unit 82 is a so-called database which stores the radiographic image received from the console 16 so as to be associated with, for example, an imaging menu or information related to the subject.

The I/F unit 84 has a function of transmitting and receiving various kinds of information to and from the console 16, using wireless communication or wired communication.

As illustrated in FIG. 19, the mammography apparatus 12 according to this embodiment differs from the mammography apparatus 12 (see FIG. 4) according to the first embodiment in that it comprises an image analysis unit 32.

The image analysis unit 32 has a function of specifying the size of the breast from a captured radiographic image of the breast. In this embodiment, the size of the breast specified by the image analysis unit 32 is not represented by a specific numerical value and means the size classification of the breast, such as a "large" size, a "normal" size, or a "small" size.

In this embodiment, in a case in which there is a radiographic image (hereinafter, referred to as a "past image") of the breast captured in the past, the size of the breast is specified from the past image. In a case in which there is no past image, the size of the breast is specified from a radiographic image (hereinafter, referred to as a "pre-image") obtaining by pre-irradiating the breast with the radiation R from the radiation source 24 for the period for which the breast is continuously compressed with the first compression pressure. Therefore, the image analysis unit 32 analyzes the past image or the pre-image. The past image and the pre-image are generically referred to as radiographic images.

A method for specifying the size of the breast using image analysis in the image analysis unit 32 is not particularly limited. For example, JP2010-253245A discloses a technique that separates a region including the breast and a region (a so-called unexposed region) which does not include the breast, on the basis of the values of pixels in a radiographic image. The size of the breast may be specified on the basis of the area of the region including the breast which is obtained by the technique.

As illustrated in FIG. 19, the mammography apparatus 12 according to this embodiment differs from the mammography apparatus 12 (see FIG. 4) according to the first embodiment in that the information 43 indicating the correspondence relationship between the type of breast and the second compression pressure is stored in the storage unit 42 in advance, as in the mammography apparatus 12 according to the second embodiment.

As described above, as the size of the breast increases, a reaction force from the breast to the compression plate 28 increases and the breast is less likely to be squeezed. Therefore, as the size of the breast increases, the mammography apparatus 12 according to this embodiment increases the second compression pressure to appropriately compress the breast.

In the mammography apparatus 12 according to this embodiment, in information 43C indicating the correspondence relationship between the size of the breast and the second compression pressure illustrated in FIG. 20 which is used as the information 43 indicating the correspondence relationship between the type of breast and the second compression pressure which is stored in the storage unit 42, the correspondence relationship between the size of the breast and the second compression pressure is shown. In the example illustrated in FIG. 20, in a case in which the size of the breast is a "large" size larger than a normal size, the second compression pressure is 0.016 N/mm$^2$. In a case in which the size of the breast is the "normal" size, the second compression pressure is 0.014 N/mm$^2$. In which the size of the breast is a "small" size less than the normal value, the second compression pressure is 0.012 N/mm$^2$.

It goes without saying that the information 43C indicating the correspondence relationship between the size of the breast and the second compression pressure is not limited to that illustrated in FIG. 20. For example, in the second embodiment, as described with reference to FIG. 13B, information indicating the correspondence relationship between the size of the breast and the difference between the second compression pressure and the reference value may be used. As described with reference to FIG. 13C, information indicating the correspondence relationship between the size of the breast and the percentage of the second compression pressure with respect to the reference value may be used. For example, the size of the breast may be classified into two stages or four or more stages.

In this embodiment, the console 16 of the radiography system 10 inquires of the image storage system 18 whether there is a past image. In a case in which there is a past image, the console 16 acquires the past image from the image storage system 18 and transmits an imaging start instruction, an imaging menu, and the past image to the mammography apparatus 12.

Figure 21:
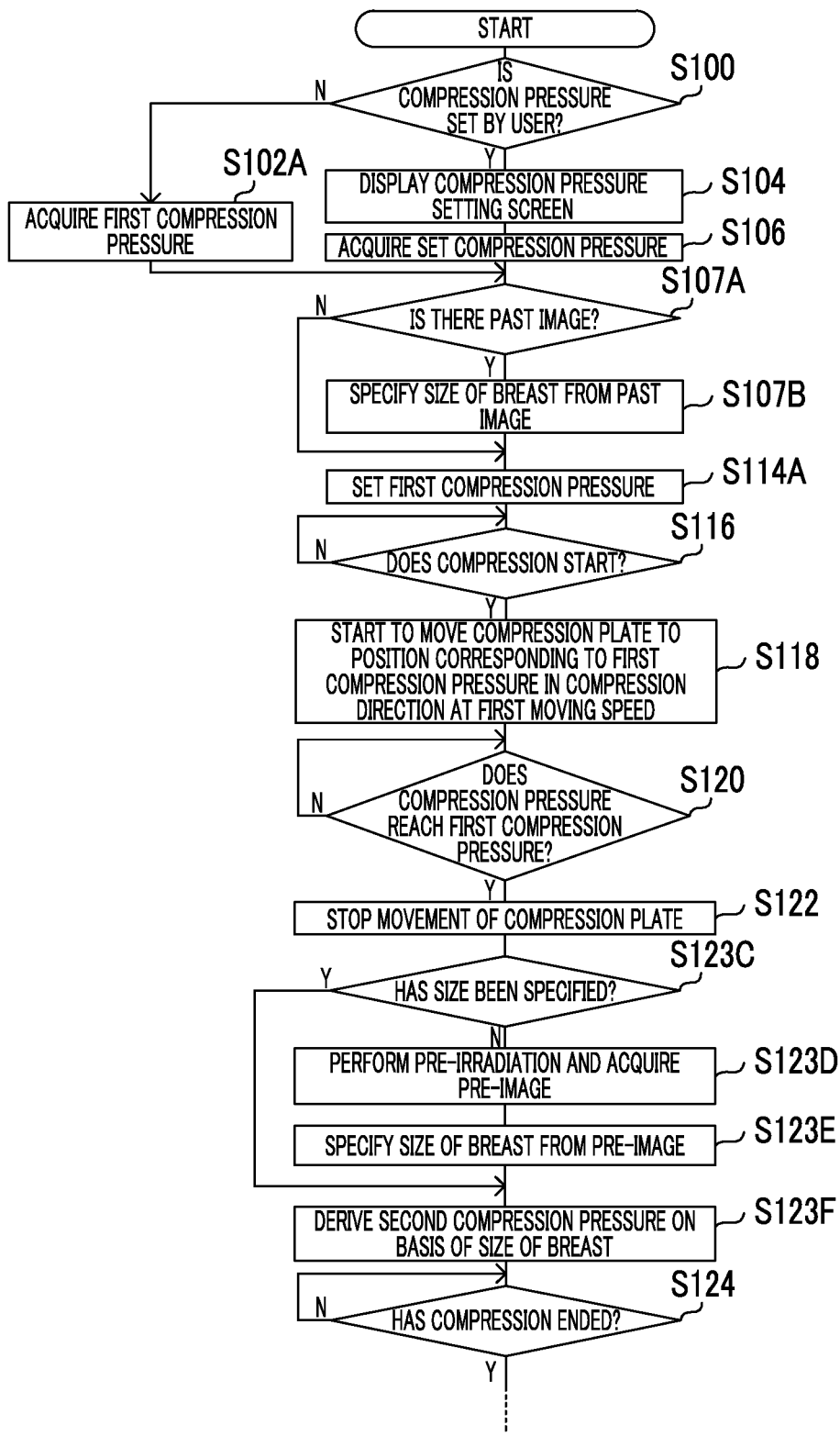
FIG. 21 is a flowchart illustrating an imaging process performed by a mammography apparatus according to the fourth embodiment.

In the mammography apparatus 12 according to this embodiment, as described above, the second compression pressure corresponds to the size of the breast. Therefore, as illustrated in FIG. 21, an imaging process performed by the control unit 40 of the mammography apparatus 12 according to this embodiment differs from the imaging process (see FIG. 9) performed by the control unit 40 of the mammography apparatus 12 according to the first embodiment in a process related to the acquisition (derivation) of the second compression pressure.

That is, the imaging process performed by the control unit 40 according to this embodiment differs from the imaging process according to the first embodiment in that it includes Step S102A instead of Step S102 according to the first embodiment and includes Steps S107A and S107B after Step S102A and Step S106. In addition, the imaging process performed by the control unit 40 according to this embodiment differs from the imaging process according to the first embodiment in that it includes Step S114A instead of Step S114 according to the first embodiment and does not include Steps S108 to S112.

In Step S102A, the control unit 40 acquires only the first compression pressure, as in the imaging process according to the second embodiment.

In Step S107A, the control unit 40 determines whether there is a past image. In a case in which no past images are received from the console 16, the determination result is "No" and the process proceeds to Step S114A. On the other hand, in a case in which a past image is received, the determination result is "Yes" and the process proceeds to Step S107B.

In Step S107B, the control unit 40 directs the image analysis unit 32 to specify the size of the breast from the past image.

Then, in Step S114A, the control unit 40 sets the first compression pressure as a target value in the moving unit 30, as in the imaging process according to the second embodiment.

In addition, the imaging process performed by the control unit 40 according to this embodiment differs from the imaging process according to the first embodiment in that it includes Steps S123C to 123F between Step S122 and Step S124.

In Step S123C, the control unit 40 determines whether the size of the breast has been specified. In a case in which the size of the breast has been specified, specifically, in a case in which the determination result in Step S107A is "Yes" and Step S107B is performed, the determination result in this step is "Yes" and the process proceeds to Step S123F. On the other hand, in a case in which the size of the breast has not been specified, specifically, in a case in which the determination result in Step S107A is "No", the determination result in this step is "No" and the process proceeds to Step S123D.

In Step S123D, the control unit 40 directs the radiation source 24 to emit the radiation R to perform pre-irradiation and acquires a pre-image. The time when the pre-irradiation is performed corresponds to an irradiation start instruction from the user, similarly to the time when the radiation R is emitted in Step S132. The dose of the radiation R emitted in the pre-irradiation may be set such that image quality which is as high as the image analysis unit 32 can specify the size of the breast is obtained and is less than the dose of the radiation R emitted in a case in which a radiographic image is captured in Step S132.

In this step, the breast compressed by the first compression pressure is irradiated with the radiation R and a pre-image which is generated on the basis of the radiation R detected by the radiation detector 22 is acquired.

Then, in Step S123E, the control unit 40 directs the image analysis unit 32 to specify the size of the breast from the pre-image.

Then, in Step S123F, the control unit 40 derives the second compression pressure on the basis of the size of the breast and the information 43C indicating the correspondence relationship between the size of the breast and the second compression pressure.

It goes without saying that a method for specifying the size of the breast is not limited to this embodiment. For example, the size of the breast may be specified from images other than a captured radiographic image of the breast. In this case, for example, an optical camera may be provided in the vicinity of a collimator (not illustrated) of the radiation source 24 and the image analysis unit 32 may perform the same image analysis as described above for an image captured by the optical camera to specify the size of the breast.

Fifth Embodiment

In this embodiment, a case in which the breast is compressed by the second compression pressure corresponding to mammary gland density as the type of breast will be described. In this embodiment, a case in which the control unit 40 specifies the magnitude of mammary gland density from a captured radiographic image of the breast will be described.

A radiography system 10 according to this embodiment has the same structure as the radiography system 10 (see FIG. 19) according to the fourth embodiment except for the following.

An image analysis unit 32 according to this embodiment has a function of specifying mammary gland density from a captured radiographic image of the breast. In this embodiment, the mammary gland density specified by the image analysis unit 32 is not represented by a specific numerical value and means mammary gland density classification, such as a "high" value, a "normal" value, or a "low" value.

In this embodiment, similarly to the fourth embodiment, in a case in which there is a past image, mammary gland density is specified from the past image. In a case in which there is no past image, mammary gland density is specified from a pre-image.

A method for specifying mammary gland density using image analysis in the image analysis unit 32 is not particularly limited. For example, a technique disclosed in JP2010-253245A which estimates mammary gland content on the basis of a radiographic image and a fat image estimated from the radiographic image may be used.

Figures 22, 23:
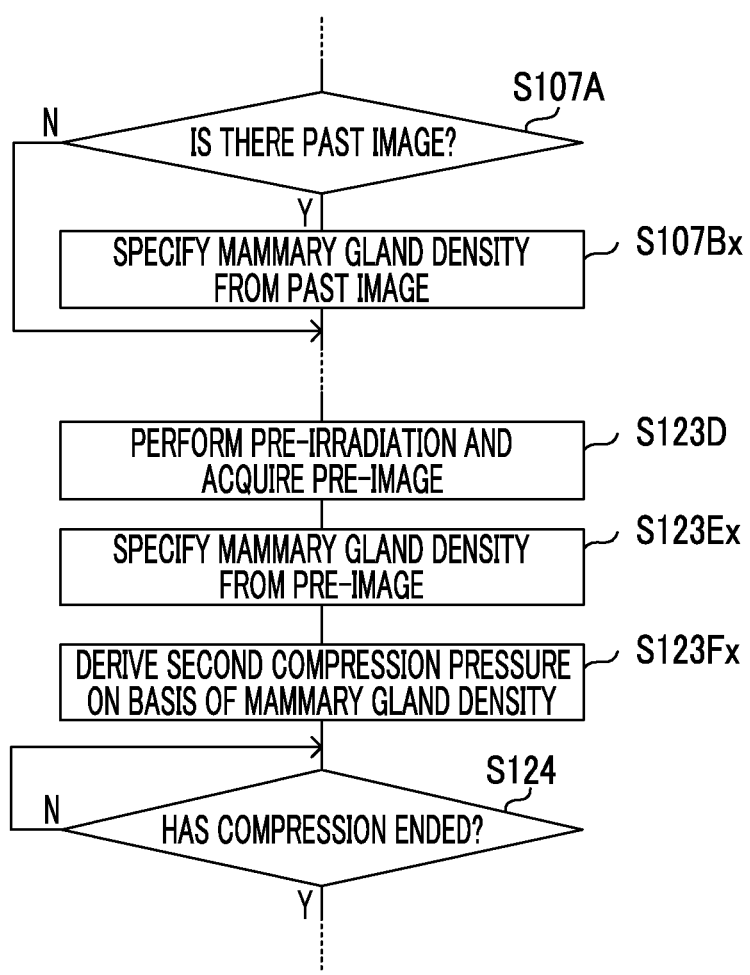
FIG. 22 is a diagram schematically illustrating an example of information indicating the correspondence relationship between mammary gland density and the second compression pressure.
FIG. 23 is a flowchart illustrating an imaging process performed by a mammography apparatus according to a fifth embodiment.

As the information 43 indicating the correspondence relationship between the type of breast and the second compression pressure, information 43D indicating the correspondence relationship between mammary gland density and the second compression pressure which is illustrated in FIG. 22 is stored in the storage unit 42 of the mammography apparatus 12 according to this embodiment. In the information 43D indicating the correspondence relationship between mammary gland density and the second compression pressure which is illustrated in FIG. 22, the correspondence relationship between mammary gland density and the second compression pressure is shown.

As mammary gland density increases, a reaction force from the breast to the compression plate 28 increases and the breast is less likely to be squeezed. Therefore, as mammary gland density increases, the mammography apparatus 12 according to this embodiment increases the second compression pressure to appropriately compress the breast. In an example of the information 43D indicating the correspondence relationship between mammary gland density and the second compression pressure which is illustrated in FIG. 22, in a case in which mammary gland density is a "high" value greater than a normal value, the second compression pressure is 0.016 N/mm$^2$. In a case in which mammary gland density is the "normal" value, the second compression pressure is 0.014 N/mm$^2$. In a case in which mammary gland density is a "low" value less than the normal value, the second compression force pressure is 0.012 N/mm$^2$.

It goes without saying that the information 43D indicating the correspondence relationship between mammary gland density and the second compression pressure is not limited to that illustrated in FIG. 22. For example, as described in the second embodiment with reference to FIG. 13B, information indicating the correspondence relationship between mammary gland density and the difference between the second compression pressure and the reference value may be used. As described with reference to FIG. 13C, information indicating the correspondence relationship between mammary gland density and the percentage of the second compression pressure with respect to the reference value may be used. For example, mammary gland density may be classified into two stages or four or more stages.

An imaging process performed by the control unit 40 of the mammography apparatus 12 according to this embodiment is the same as the imaging process (see FIG. 21) performed by the control unit 40 of the mammography apparatus 12 according to the fourth embodiment except that mammary gland density is applied instead of the size of the breast.

That is, as illustrated in FIG. 23, the imaging process performed by the control unit 40 according to this embodiment includes Step S107Bx, Step S123Ex, and Step S123Fx instead of Step S107B, Step S123E, and Step S123F in the imaging process performed by the control unit 40 according to the fourth embodiment.

In Step S107Bx, the control unit 40 directs the image analysis unit 32 to specify mammary gland density from a past image.

In Step S123Ex, the control unit 40 directs the image analysis unit 32 to specify mammary gland density from a pre-image.

Then, in Step S123Fx, the control unit 40 derives the second compression pressure on the basis of the mammary gland density and the information 43D indicating the correspondence relationship between the mammary gland density and the second compression pressure.

It goes without saying that a method for specifying mammary gland density is not limited to that in this embodiment. For example, the image analysis unit 32 may execute mammary gland density three-dimensional evaluation software, such as Volpara (registered trademark), to specify mammary gland density. In addition, for example, a technique disclosed in JP2012-135444A which detects the proportion of a white region to a predetermined region as mammary gland density on the basis of the pixel value of a radiographic image may be applied to specify mammary gland density.

Sixth Embodiment

In this embodiment, a case in which the breast is compressed by the second compression pressure corresponding to the hardness of the breast as the type of breast will be described.

A radiography system 10 according to this embodiment has the same structure as the radiography system 10 (see FIG. 4) according to the first embodiment except for the following.

The information 43 indicating the correspondence relationship between the type of breast and the second compression pressure is stored in the storage unit 42 of the mammography apparatus 12 according to this embodiment, similarly to the storage unit 42 (see FIG. 12) of the mammography apparatus 12 according to the second embodiment.

In general, as the hardness of the breast increases, the subject's pain in a case in which the breast is compressed tends to increase. Therefore, as the hardness of the breast increases, the mammography apparatus 12 according to this embodiment decreases the second compression pressure to appropriately and effectively reduce the subject's pain.

In the mammography apparatus 12 according to this embodiment, as the information 43 indicating the correspondence relationship between the type of breast and the second compression pressure, information 43E indicating the correspondence relationship between the hardness of the breast and the second compression pressure which is illustrated in FIG. 24 is stored in the storage unit 42.

In an example of the information 43E indicating the correspondence relationship between the hardness of the breast and the second compression pressure which is illustrated in FIG. 24, in a case in which the hardness of the breast is a "low" value less than a normal value, the second compression pressure is $0.016$ N/mm$^2$. In a case in which the hardness of the breast is the "normal" value, the second compression pressure is $0.014$ N/mm$^2$. In a case in which the hardness of the breast is a "high" value greater than the normal value, the second compression pressure is $0.012$ N/mm$^2$.

It goes without saying that the information 43E indicating the correspondence relationship between the hardness of the breast and the second compression pressure is not limited to that illustrated in FIG. 24. For example, as described in the second embodiment with reference to FIG. 13B, information indicating the correspondence relationship between the hardness of the breast and the difference between the second compression pressure and the reference value may be used. As described with reference to FIG. 13C, information indicating the correspondence relationship between the hardness of the breast and the percentage of the second compression pressure with respect to the reference value may be used. For example, the hardness of the breast may be classified into two stages or four or more stages.

An imaging process performed by the control unit 40 of the mammography apparatus 12 according to this embodiment is the same as the imaging process (see FIG. 14) performed by the control unit 40 of the mammography apparatus 12 according to the second embodiment except that the hardness of the breast is applied instead of the thickness of the breast.

That is, as illustrated in FIG. 25, the imaging process performed by the control unit 40 according to this embodiment includes Step S123Ax and Step S123Bx, instead of Step S123A and Step S123B in the imaging process performed by the control unit 40 according to the second embodiment.

In Step S123Ax, the control unit 40 specifies the hardness of the breast. In general, as the hardness of the breast increases, a variation in compression pressure per unit time is reduced. Therefore, the control unit 40 calculates a variation in compression pressure over time (compression pressure/time) in the movement of the compression plate 28 from an initial position to a position corresponding to the first compression pressure and specifies the hardness of the breast on the basis of the calculation result. In this embodiment, the hardness of the breast is specified depending on which of the classifications of the "low" value, the "normal" value, and the "high" value the calculated variation in compression pressure over time corresponds to.

Then, in Step S123Bx, the control unit 40 derives the second compression pressure on the basis of the hardness of the breast and the information 43E indicating the correspondence relationship between the hardness of the breast and the second compression pressure.

It goes without saying that a method for specifying the hardness of the breast is not limited to that in this embodiment. For example, in general, in a case in which a variation in compression pressure per unit time is constant, as the hardness of the breast increases, the amount of movement of the compression plate 28 per unit time is reduced. Therefore, similarly to the mammography apparatus 12 according to the second embodiment, the mammography apparatus 12 may comprise a movement amount detection unit 31 and the control unit 40 may calculate the amount of movement per unit time on the basis of the result obtained by moving the compression plate 28 to the position corresponding to the first compression pressure, with a variation in compression pressure per unit time constant, and specify the hardness of the breast on the basis of the calculated amount of movement per unit time.

For example, a compression force detection sensor (not illustrated) that detects a reaction force from the compressed breast to the compression plate 28 as the compression force may be provided in the vicinity of the root of the compression plate 28 or in the vicinity of the root of the ball screw 37 and the control unit 40 may specify the hardness of the breast on the basis of the compression force detected by the compression force detection sensor or the amount of movement of the compression plate 28.

Seventh Embodiment

In this embodiment, a case in which the breast is compressed by the second compression pressure corresponding to the weight of the breast as the type of breast will be described.

Figure 26:
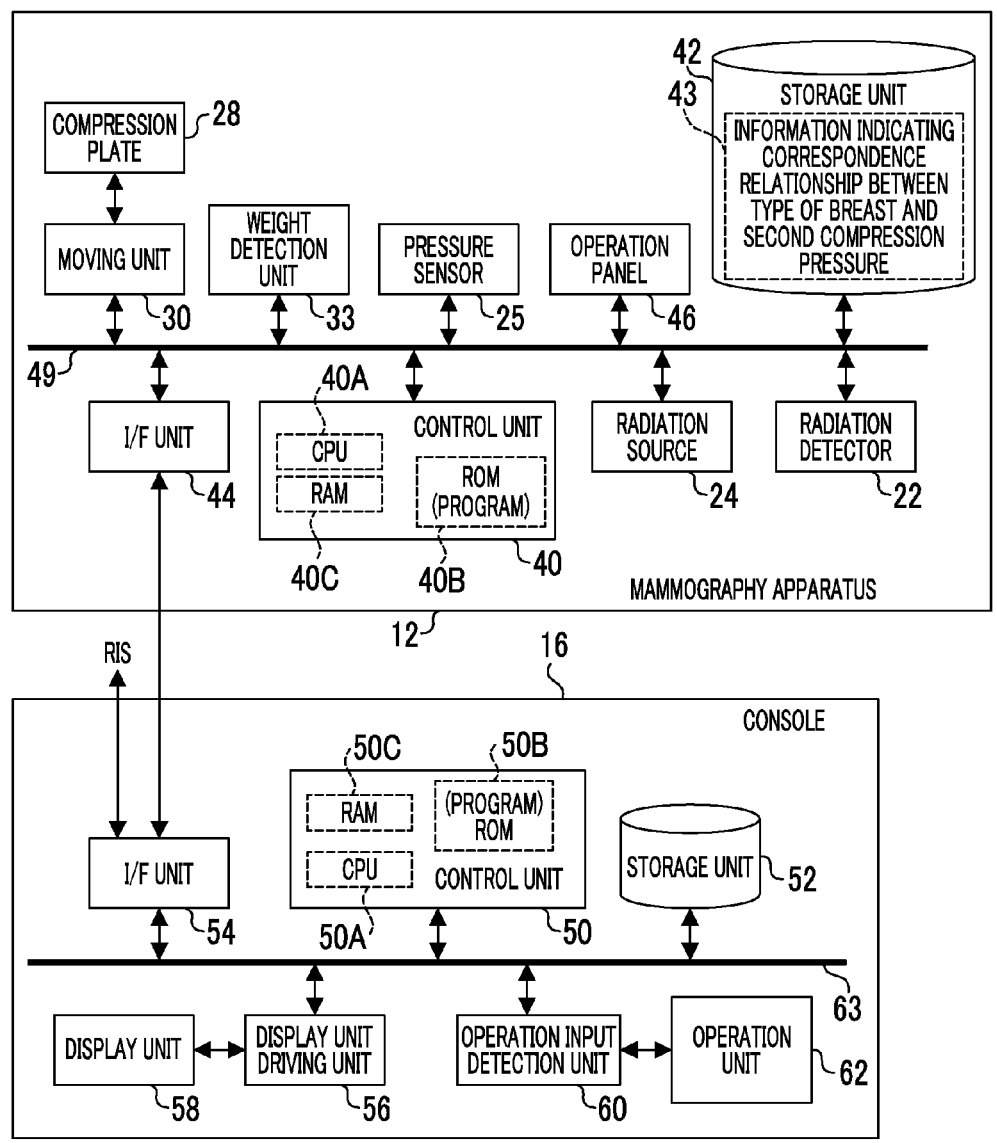
FIG. 26 is a block diagram illustrating the structure of a radiography system according to a seventh embodiment.

As illustrated in FIG. 26, a mammography apparatus 12 according to this embodiment differs from the mammography apparatus 12 (see FIG. 4) according to the first embodiment in that it comprises a weight detection unit 33.

The weight detection unit 33 has a function of detecting the weight of the breast. A method for detecting the weight of the breast is not particularly limited. For example, the weight detection unit 33 may be provided as a weight sensor, such as a strain gauge, in the imaging stand 26 and may detect the weight of the breast positioned on the imaging surface 27 of the imaging stand 26.

As the information 43 indicating the correspondence relationship between the type of breast and the second compression pressure, information 43F indicating the correspondence relationship between the weight of the breast and the second compression pressure which is illustrated in FIG. 27 is stored in the storage unit 42 of the mammography apparatus 12 according to this embodiment. In the information 43F indicating the correspondence relationship between the weight of the breast and the second compression pressure which is illustrated in FIG. 27, the correspondence relationship between the weight of the breast and the second compression pressure is shown.

In general, the weight of the breast is associated with the size of the breast. As the weight of the breast increases, the size of the breast increases. As described above, as the size of the breast increases, a reaction force from the breast to the compression plate 28 increases and the breast is less likely to be squeezed. Therefore, as the weight of the breast increases, the mammography apparatus 12 according to this embodiment increases the second compression pressure to appropriately compress the breast.

In the example illustrated in FIG. 27, in a case in which the weight of the breast is a "large" value greater than a normal value, the second compression pressure is 0.016 $N/mm^2$. In a case in which the weight of the breast is the "normal" value, the second compression pressure is 0.014 $N/mm^2$. In a case in which the weight of the breast is a "small" value less than the normal value, the second compression pressure is 0.012 $N/mm^2$.

It goes without saying that the information 43F indicating the correspondence relationship between the weight of the breast and the second compression pressure is not limited to that illustrated in FIG. 27. For example, as described in the second embodiment with reference to FIG. 13B, information indicating the correspondence relationship between the weight of the breast and the difference between the second compression pressure and the reference value may be used. As described with reference to FIG. 13C, information indicating the correspondence relationship between the weight of the breast and the percentage of the second compression pressure with respect to the reference value may be used. For example, the weight of the breast may be classified into two stages or four or more stages.

Figure 28:
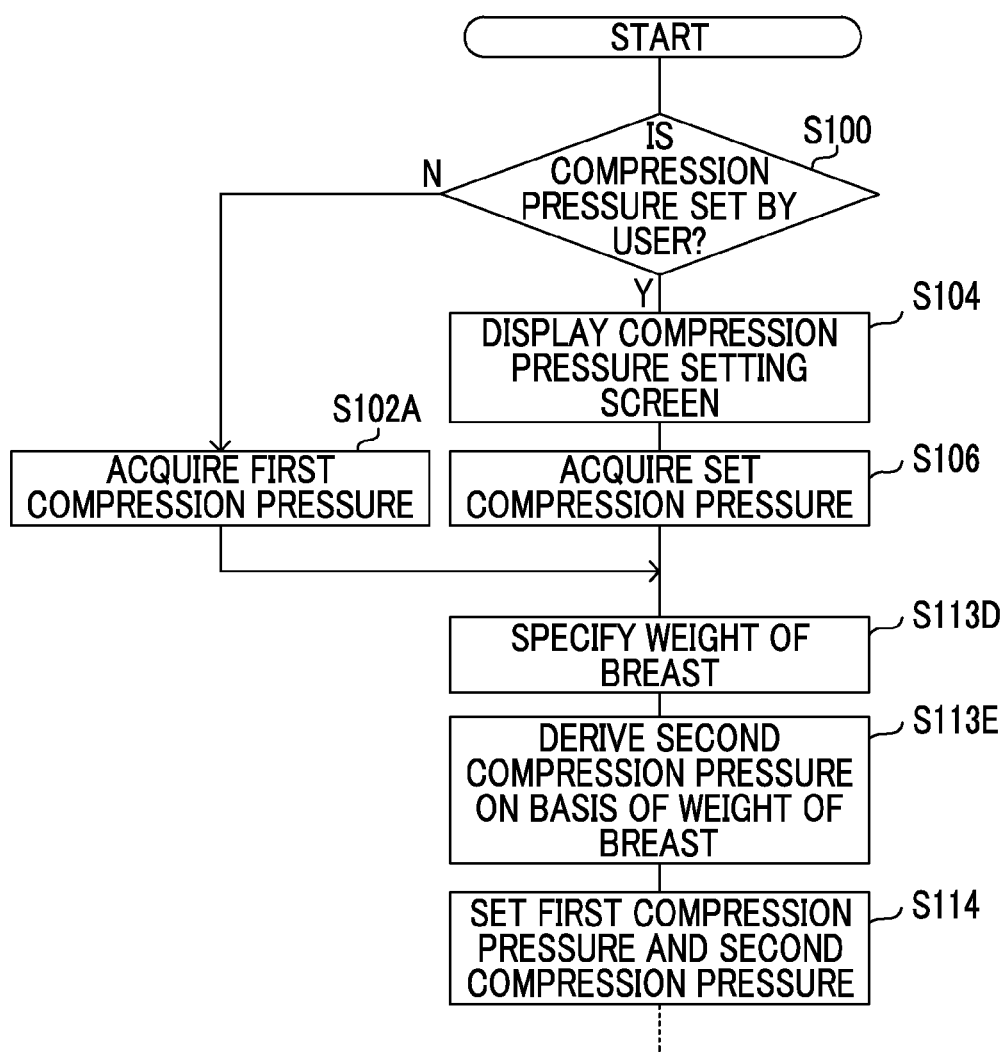
FIG. 28 is a flowchart illustrating an imaging process performed by a mammography apparatus according to the seventh embodiment.

In the mammography apparatus 12 according to this embodiment, as described above, the second compression pressure corresponds to the weight of the breast. Therefore, as illustrated in FIG. 28, an imaging process performed by the control unit 40 of the mammography apparatus 12 according to this embodiment differs from the imaging process (see FIG. 9) performed by the control unit 40 of the mammography apparatus 12 according to the first embodiment in a process related to the acquisition (derivation) of the second compression pressure.

That is, the imaging process performed by the control unit 40 according to this embodiment differs from the imaging process according to the first embodiment in that it includes Step S102A instead of Step S102 according to the first embodiment, includes Step S113D and Step S113E before Step S114, and does not include Steps S108 to S112.

In Step S102A, the control unit 40 acquires only the first compression pressure, as in the imaging process according to the second embodiment.

In Step S113D, the control unit 40 specifies the weight of the breast on the basis of the detection result of the weight detection unit 33. In this embodiment, the weight of the breast is specified depending on which of the classifications of the "large" value, the "normal" value, and the "small" value the detection result corresponds to.

Then, in Step S113E, the control unit 40 derives the second compression pressure on the basis of the weight of the breast and the information 43F indicating the correspondence relationship between the weight of the breast and the second compression pressure.

It goes without saying that a method for specifying the weight of the breast is not limited to that in this embodiment. For example, the user may set the weight of the breast through the operation panel 46.

Eighth Embodiment

In the first to seventh embodiments, the case in which, after the compression plate 28 is moved to the position corresponding to the first compression pressure in the compression direction, the movement of the compression plate 28 in the decompression direction starts according to whether the compression of the breast by the first compression pressure is maintained for a predetermined period of time has been described. However, the time when the movement of the compression plate 28 in the decompression direction starts is not limited thereto.

For example, the control unit 40 of the mammography apparatus 12 may start the movement of the compression plate 28 in the decompression direction on the basis of a movement instruction which is input by the user through a movement instruction operation unit, such as the operation panel 46 of the mammography apparatus 12 or the operation unit 62 of the console 16.

Figure 29:
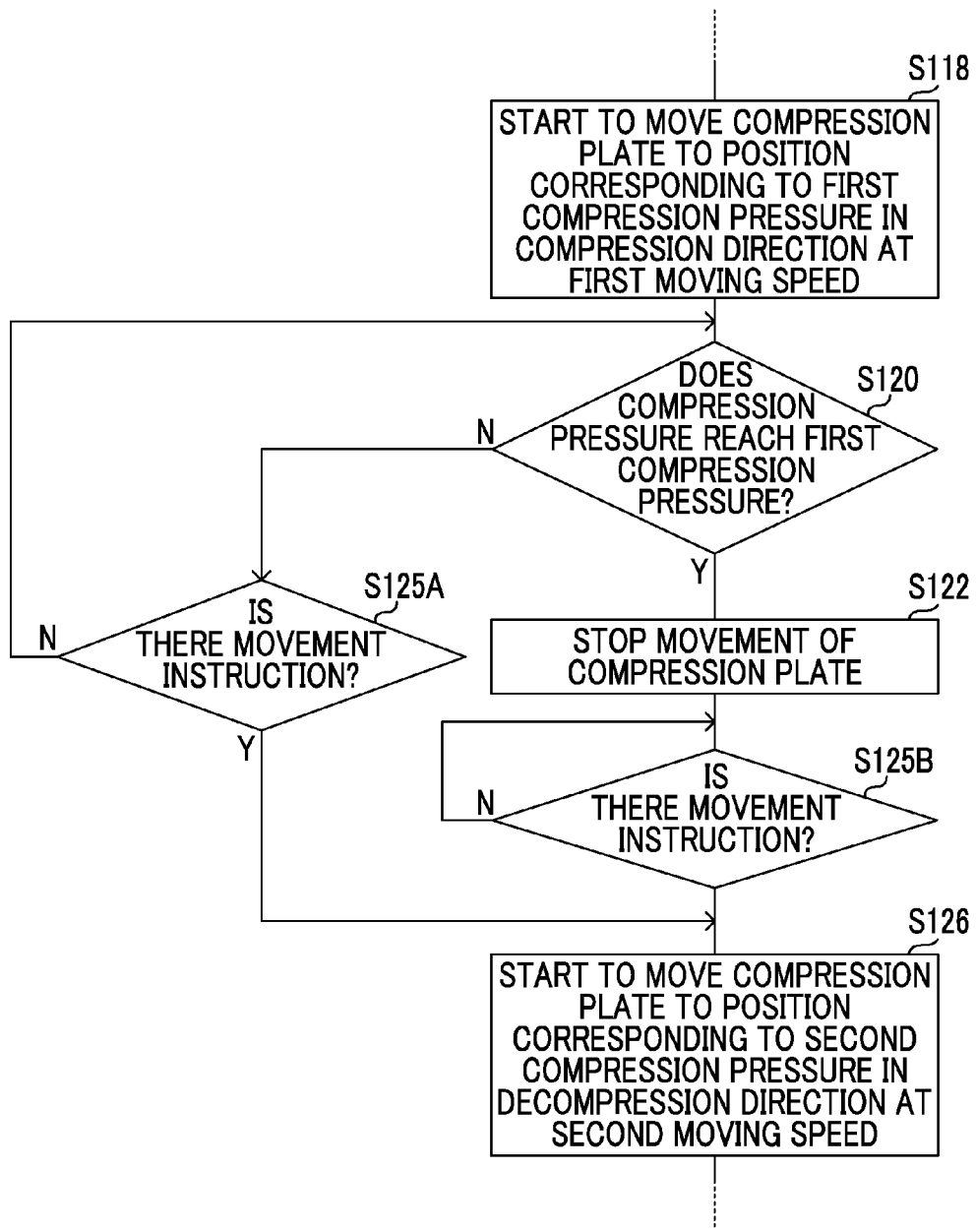
FIG. 29 is a flowchart illustrating an imaging process performed by a mammography apparatus according to an eighth embodiment in a case in which the movement of the compression plate in a decompression direction starts in response to a movement instruction from a user.

In this case, as illustrated in FIG. 29, an imaging process performed by the control unit 40 of the mammography apparatus 12 according to this embodiment differs from the imaging process (see FIG. 9) performed by the control unit 40 of the mammography apparatus 12 according to the first embodiment in a process after the movement of the compression plate 28 in the compression direction starts.

That is, the imaging process performed by the control unit 40 according to this embodiment differs from the imaging process according to the first embodiment in that it includes Step S125A and Step S125B before Step S126 according to the first embodiment.

As illustrated in FIG. 29, in a case in which the determination result in Step S120 is "No", the process proceeds to Step S125A. Then, in Step S125A, the control unit 40 determines whether the movement start instruction has been input from the user. In a case in which the movement start instruction has not been input, the determination result is "No" and the process returns to Step S120.

In a case in which the user wants to move the compression plate 28 in the decompression direction, for example, in a case in which the subject feels a severe pain, an instruction to start the movement of the compression plate 28 in the decompression direction may be input even before the compression pressure to compress the breast reaches the first compression pressure. In this case, since the movement start instruction is input, the determination result in Step S125A is "Yes" and the process proceeds to Step S126. The movement of the compression plate 28 in the decompression direction starts.

On the other hand, in a case in which the determination result in Step S120 is "Yes", the process proceeds to Step 122 and the movement of the compression plate 28 is stopped. Then, the process proceeds to Step S125B.

In Step S125B, the control unit 40 determines whether the movement start instruction has been input from the user. In a case in which the movement start instruction has not been input, the determination result is "No" and the control unit 40 is in a standby state. On the other hand, in a case in which the movement start instruction has been input, the determination result is "Yes" and the process proceeds to Step S126. The movement of the compression plate 28 in the decompression direction starts.

As another example of the time when the movement of the compression plate 28 in the decompression direction starts, for example, in a case in which the compression pressure derived by the control unit 40 reaches the first compression pressure, the control unit 40 of the mammography apparatus 12 may start the movement of the compression plate 28 in the decompression direction. That is, the control unit 40 may perform control such that the time for which the compression of the breast by the first compression pressure is maintained is 0.

Figure 30:
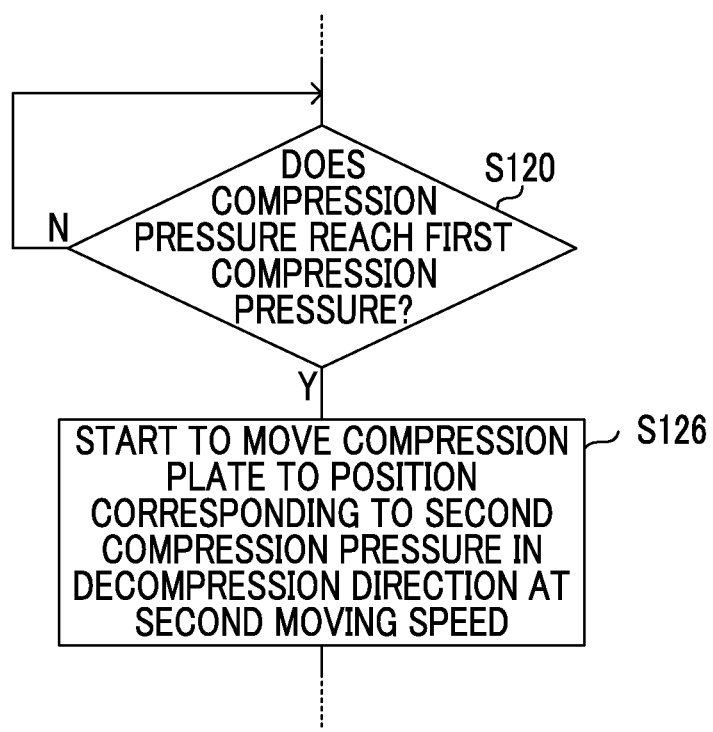
FIG. 30 is a flowchart illustrating an imaging process performed by the mammography apparatus according to the eighth embodiment in a case in which, when the compression pressure detected by a compression force detection sensor reaches a first compression pressure, the movement of the compression plate in the decompression direction starts.

In this case, as illustrated in FIG. 30, in the imaging process performed by the control unit 40 of the mammography apparatus 12 according to this embodiment, in a case in which the determination result in Step S120 is "Yes", the process may proceed to Step S126, without performing Step S122 and Step S124, and the movement of the compression plate 28 in the decompression direction may start.

As such, the time when the control unit 40 stops the compression plate 28 moved from the initial position in the compression direction or the time when the control unit 40 starts the movement of the compression plate 28 in the decompression direction is not limited to the above. For example, when the breast is compressed to some degree, a variation in compression pressure is reduced and the thickness of the breast changes little. Therefore, the control unit 40 may derive a variation in the compression pressure applied to the breast by the compression plate 28, which has started to move from the initial position, on the basis of the detection results of the pressure sensors 25 provided in the mammography apparatus 12 according to the first embodiment. In a case in which the variation in the compression pressure is less than a predetermined value (for example, 0.002 N/mm$^2$), the control unit 40 may stop the movement of the compression plate 28.

Ninth Embodiment

In each of the above-described embodiments, the case in which the mammography apparatus 12 compresses the breast with the first compression pressure and the second compression pressure (two-stage compression) has been described. However, two-stage compression and a case (one-stage compression) in which the mammography apparatus 12 compresses the breast with only the first compression pressure may be switched.

For example, various types of compression plates 28 are used according to the purpose of use or the type of breast. In some cases, it is preferable to perform one-stage compression, according to the type of compression plate 28. For example, in a case in which a spot compression plate that is smaller than the size of the breast and is used for spot imaging is used, it is preferable to perform one-stage compression.

Therefore, in this embodiment, a case in which the control unit 40 of the mammography apparatus 12 prohibits two-stage compression according to the type of compression plate 28 will be described.

Figure 31:
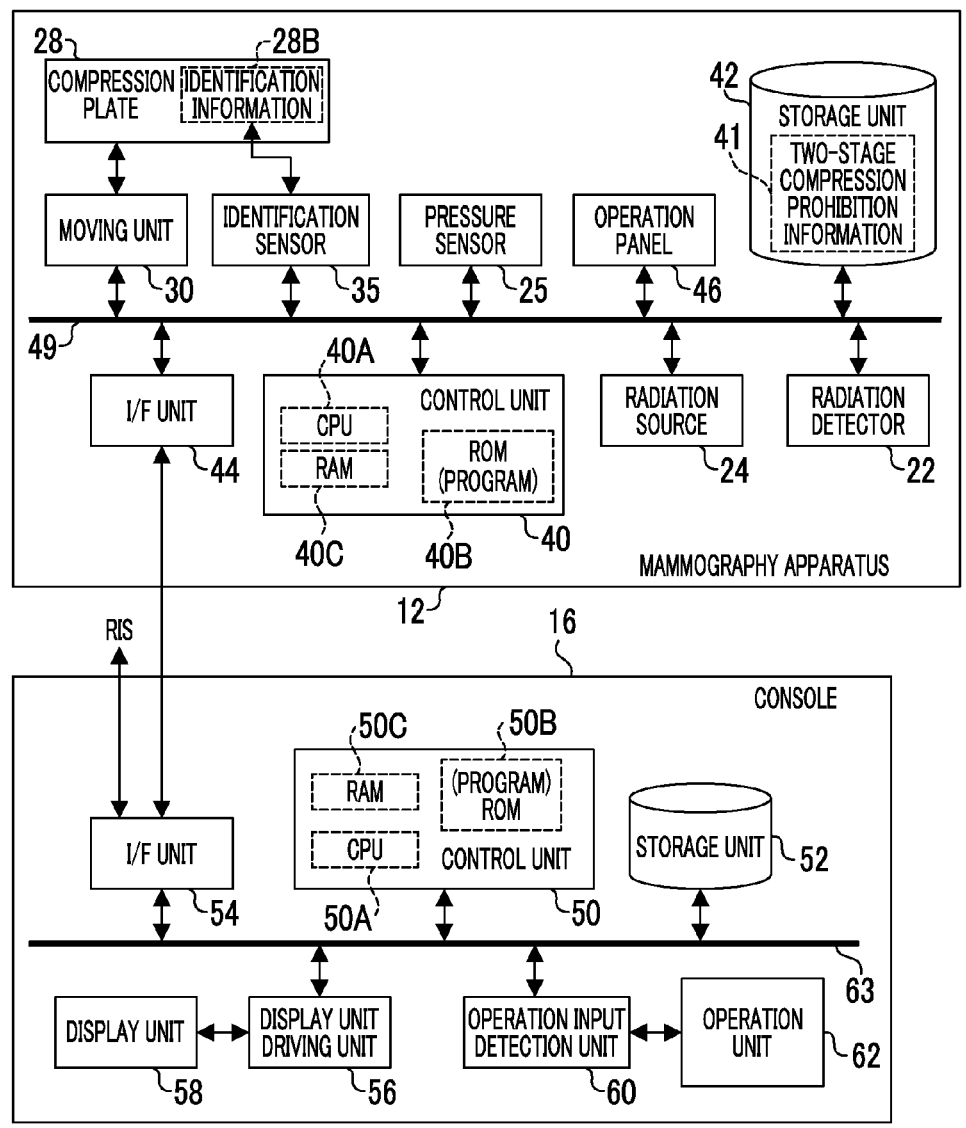
FIG. 31 is a block diagram illustrating the structure of a radiography system according to a ninth embodiment.

As illustrated in FIG. 31, the mammography apparatus 12 according to this embodiment differs from the mammography apparatus 12 (see FIG. 4) according to the first embodiment in that identification information 28B for identifying the type of compression plate is provided in the compression plate 28 and the mammography apparatus 12 comprises an identification sensor 35 for reading the identification information 28B.

Figure 32:
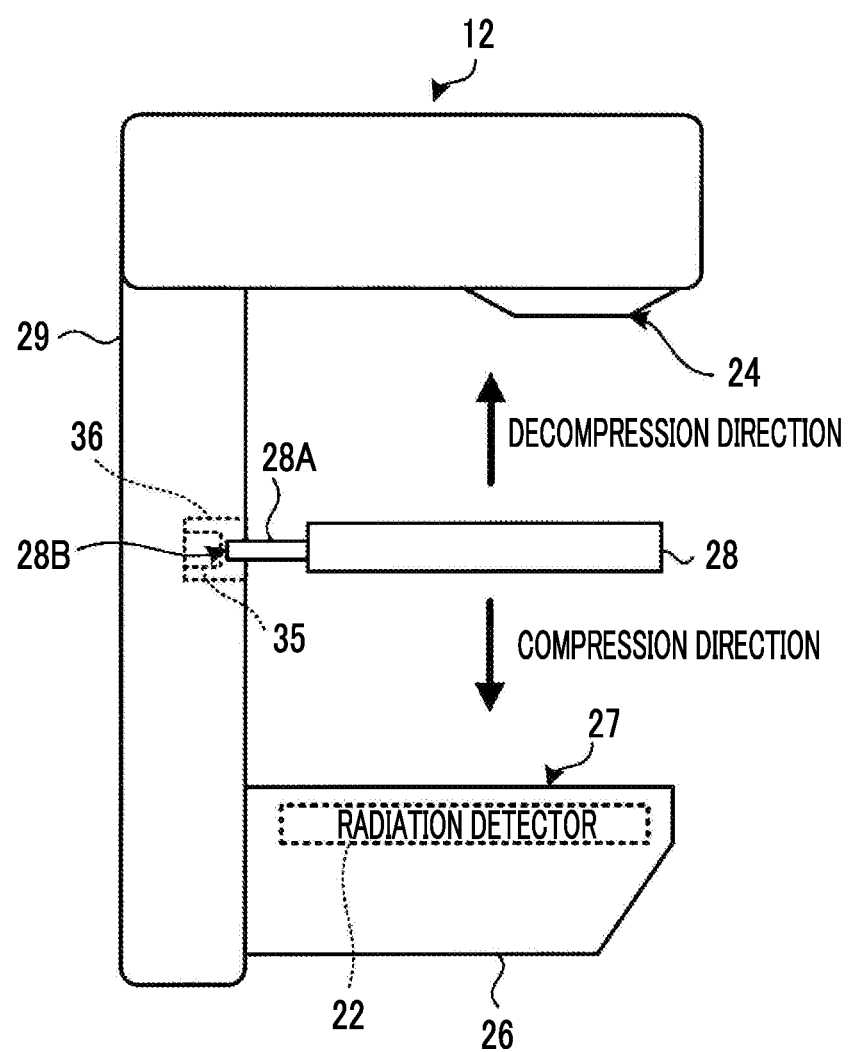
FIG. 32 is a side view illustrating a structure for identifying the type of compression plate in a mammography apparatus according to the ninth embodiment.

As illustrated in FIG. 32, the mammography apparatus 12 according to this embodiment comprises a connection portion 36 for attaching the compression plate 28 to the holding portion 29. An attachment portion 28A of the compression plate 28 is attached to the connection portion 36 to connect the compression plate 28 and the ball screw 37 (see FIG. 3). Therefore, the compression plate 28 can be moved by the moving unit 30. As illustrated in FIG. 32, the identification information 28B is provided in the attachment portion 28A of the compression plate 28 and the identification sensor 35 is provided in the connection portion 36.

The identification information 28B and the identification sensor 35 are not particularly limited. For example, a plurality of pins may be two-dimensionally provided in the attachment portion 28A and the arrangement of the pins may be used as the identification information 28B. In this case, the identification sensor 35 may be a sensor that can detect the arrangement of the pins. In addition, for example, the identification information 28B may be a detection marker corresponding to the type of compression plate. In this case, the identification sensor 35 may be a sensor, such as a photointerrupter that can detect each bit of the detection marker.

As illustrated in FIG. 31, the mammography apparatus 12 according to this embodiment differs from the mammography apparatus 12 (see FIG. 4) according to the first embodiment in that two-stage compression prohibition information 41 is stored as identification information indicating the type of compression plate that is prohibited to perform two-stage compression in the storage unit 42. In this case, the storage unit 42 corresponds to a prohibition information storage unit according to the invention and the two-stage compression prohibition information 41 corresponds to prohibition information according to the invention.

Figure 33:
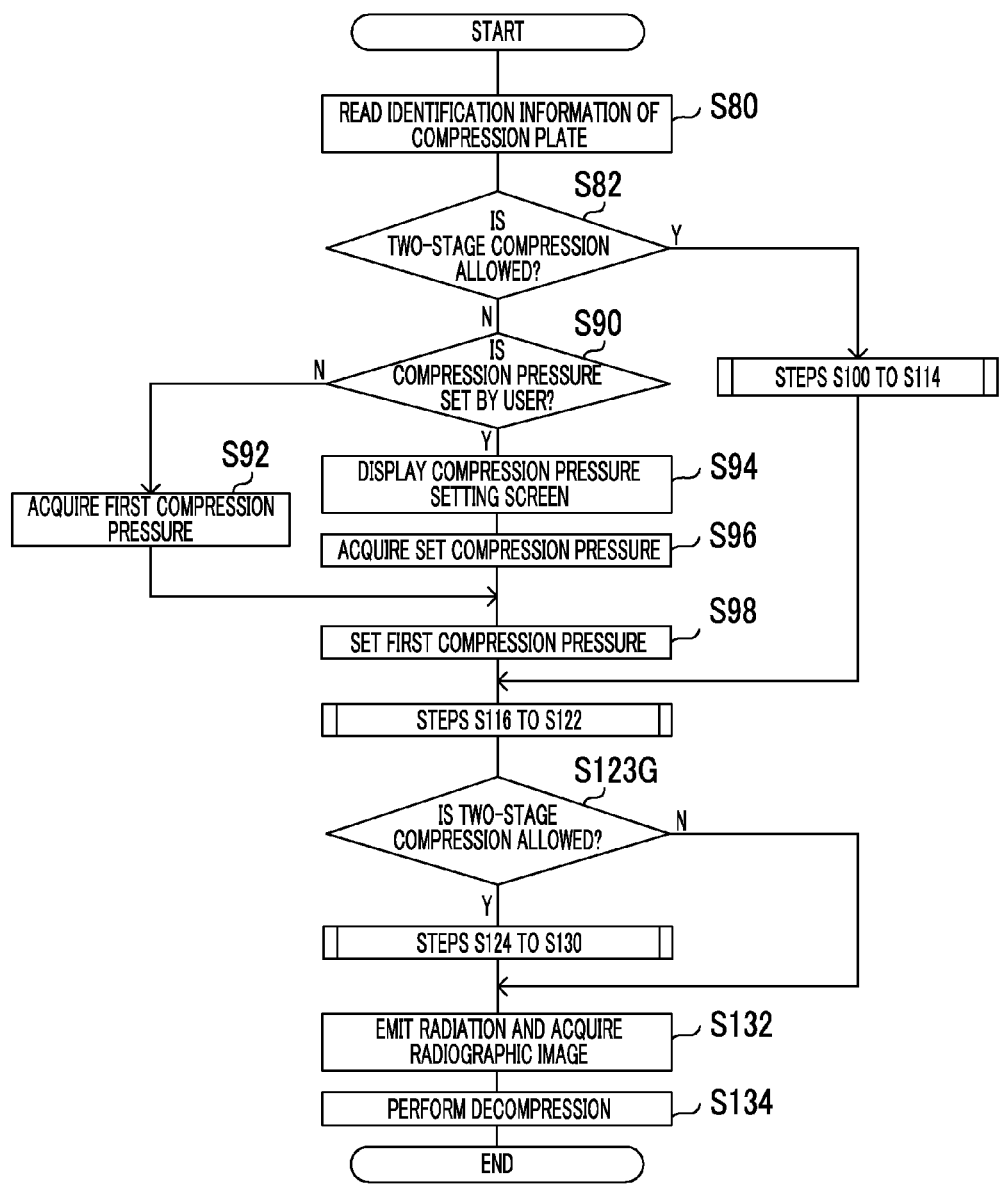
FIG. 33 is a flowchart illustrating an imaging process performed by the mammography apparatus according to the ninth embodiment.

As illustrated in FIG. 33, an imaging process performed by the control unit 40 of the mammography apparatus 12 according to this embodiment differs from the imaging process (see FIG. 9) performed by the control unit 40 of the mammography apparatus 12 according to the first embodiment in that a process which prohibits two-stage compression is performed according to the identified type of compression plate 28.

That is, the imaging process performed by the control unit 40 according to this embodiment differs from the imaging process according to the first embodiment in that, when the imaging process starts, Steps S80 to S98 are performed.

When the imaging process starts, first, in Step S80, the control unit 40 directs the identification sensor 35 to read the identification information of the compression plate 28.

Then, in Step S82, the control unit 40 determines whether two-stage compression is allowed. In this embodiment, in a case in which the read identification information is not included in the two-stage compression prohibition information 41 stored in the storage unit 42, two-stage compression is allowed and the determination result is "Yes". After Steps S100 to S114 are performed, the process proceeds to Step S116, as in the imaging process according to the first embodiment.

On the other hand, in a case in which the read identification information is included in the two-stage compression prohibition information 41 stored in the storage unit 42, two-stage compression is prohibited and the determination result is "No". The process proceeds to Step S90.

Steps S90 to S98 are similar to Steps S100 to S114 except that, since two-stage compression is prohibited, the user can set only the first compression pressure.

Specifically, in Step S90, the control unit 40 determines whether a compression pressure is set by the user. In a case in which a compression pressure setting instruction is not received from the operation panel 46 even after a predetermined period of time (10 seconds in this embodiment) elapses, the determination result is "No" and the process proceeds to Step S92.

In Step S92, the control unit 40 acquires a predetermined first compression pressure and proceeds to Step S98.

On the other hand, in a case in which a compression pressure setting instruction is received from the operation panel 46 in Step S90, the determination result is "Yes" and the process proceeds to Step S94. In Step S94, the control unit 40 displays a compression pressure setting screen (not illustrated) on the operation panel 46.

Then, in Step S96, the control unit 40 acquires the first compression pressure set by the user through the operation panel 46. Then, in Step S98, the control unit 40 sets the first compression pressure as a target value in the moving unit 30 and proceeds to Step S116.

As illustrated in FIG. 33, the imaging process performed by the control unit 40 according to this embodiment differs from the imaging process according to the first embodiment in that Step S123G is performed between Step S122 and Step S124 according to the first embodiment.

In Step S123G the control unit 40 determines whether two-stage compression is allowed. A determination method in this step is not particularly limited. For example, similarly to Step S82, the determination may be performed on the basis of the identification information 28B and the two-stage compression prohibition information 41. Alternatively, the determination result in Step S82 may be stored and may be used for the determination in Step S123G. In addition, in a case in which only the first compression pressure is set as a target value in the moving unit 30, it may be determined that two-stage compression is prohibited.

In a case in which two-stage compression is not prohibited, the determination result is "Yes" and the process proceeds to Step S124. On the other hand, in a case in which two-stage compression is prohibited, the determination result is "No" and the process proceeds to Step S132. In this case, in Step S132, the control unit 40 directs the radiation source 24 to emit the radiation R in a state in which the breast is compressed by the compression plate 28 with the first compression pressure and acquires a radiographic image.

A method of selecting one of the two-stage compression and the one-stage compression is not limited to that in this embodiment and the two-stage compression or the one-stage compression may be selected by, for example, an instruction from the user.

In a case in which the two-stage compression is performed, it is preferable to display information indicating the execution of the two-stage compression such that the user or the subject is not startled. In addition, it is preferable that the information indicating the execution of two-stage compression or the compression pressure when the radiation R is emitted is stored so as to be associated with the image data of the acquired radiographic image.

Tenth Embodiment

The moving speed of the compression plate 28 moved by the moving unit 30 under the control of the control unit 40 is not limited to the examples described in the first to ninth embodiments.

For example, in the first to ninth embodiments, the case in which the compression plate 28 is moved from the initial position to the first compression pressure at the first moving speed has been described. However, the moving speed of the compression plate 28 for this period may be changed. For example, the moving speed may be changed depending on a contact state between the breast and the compression plate 28. An example of this case will be described.

Figure 34:
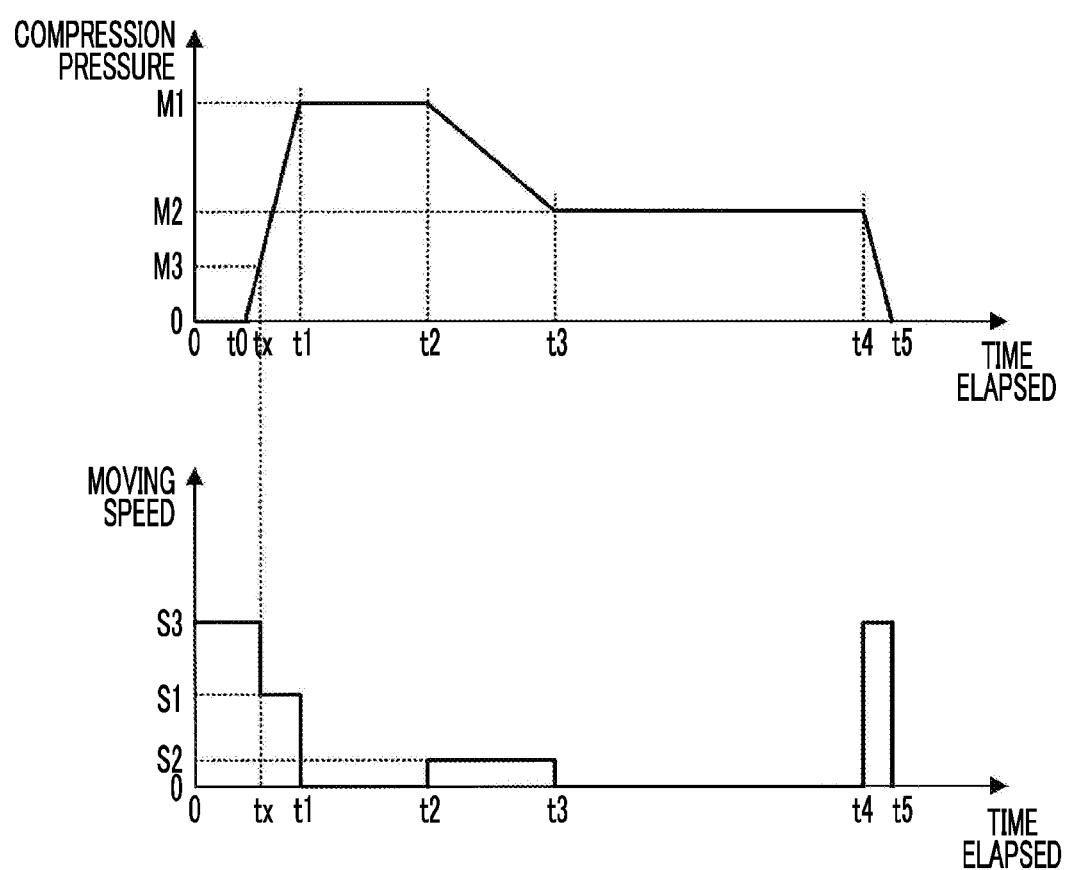
FIG. 34 is a timing chart illustrating an example of the moving speed of a compression plate in a mammography apparatus according to a tenth embodiment.

It is possible to move the compression plate 28, without considering the subject's pain caused by the compression of the breast until the compression plate 28 comes into contact with the breast. Therefore, in this embodiment, as illustrated in FIG. 34, the moving speed until the compression plate 28 comes into contact with the breast or until a compression pressure that is estimated not to inflict a severe pain on the subject is applied after the contact is higher than the moving speed until the compression pressure reaches the first compression pressure M1 after the compression plate 28 comes into contact with the breast or the estimated compression pressure is applied. In the example illustrated in FIG. 34, the control unit 40 moves the compression plate 28 at a third moving speed S3 until the compression plate 28 comes into contact with the breast at a time t0 and the compression pressure increases and reaches a third compression pressure M3. Then, the control unit 40 moves the compression plate 28 at a first moving speed S1 for a period from a time tx when the compression pressure reaches the third compression pressure M3 to a time t1, as in the first to ninth embodiments.

The first moving speed S1 and the third moving speed S3 according to this embodiment are preferably in the range of 1 mm/s to 50 mm/s which has been preferably described as the first moving speed S1 in the first embodiment. The third moving speed S3 may be higher than the first moving speed S1. The third moving speed S3 is preferably in the range of 1 mm/s to 50 mm/s and is more preferably 40 mm/s. The first moving speed S1 may be lower than the third moving speed S3. The first moving speed S1 is preferably in the range of 1 mm/s to 30 mm/s and is more preferably 10 mm/s.

The third compression pressure M3 may be determined, considering, for example, the degree of the subject's pain obtained by experiments, and is not particularly limited. For example, the third compression pressure M3 may be 0 $N/mm^2$. It is preferable that the third compression pressure M3 is greater than 0 $N/mm^2$ and is, for example, 0.007 $N/mm^2$, considering a detection error. In this embodiment, the third compression pressure M3 is set in the moving unit 30 in advance. However, the control unit 40 may derive the third compression pressure M3 according to a first compression pressure M1, a second compression pressure M2, or the type of breast and may set the third compression pressure M3 in the moving unit 30.

Figure 35:
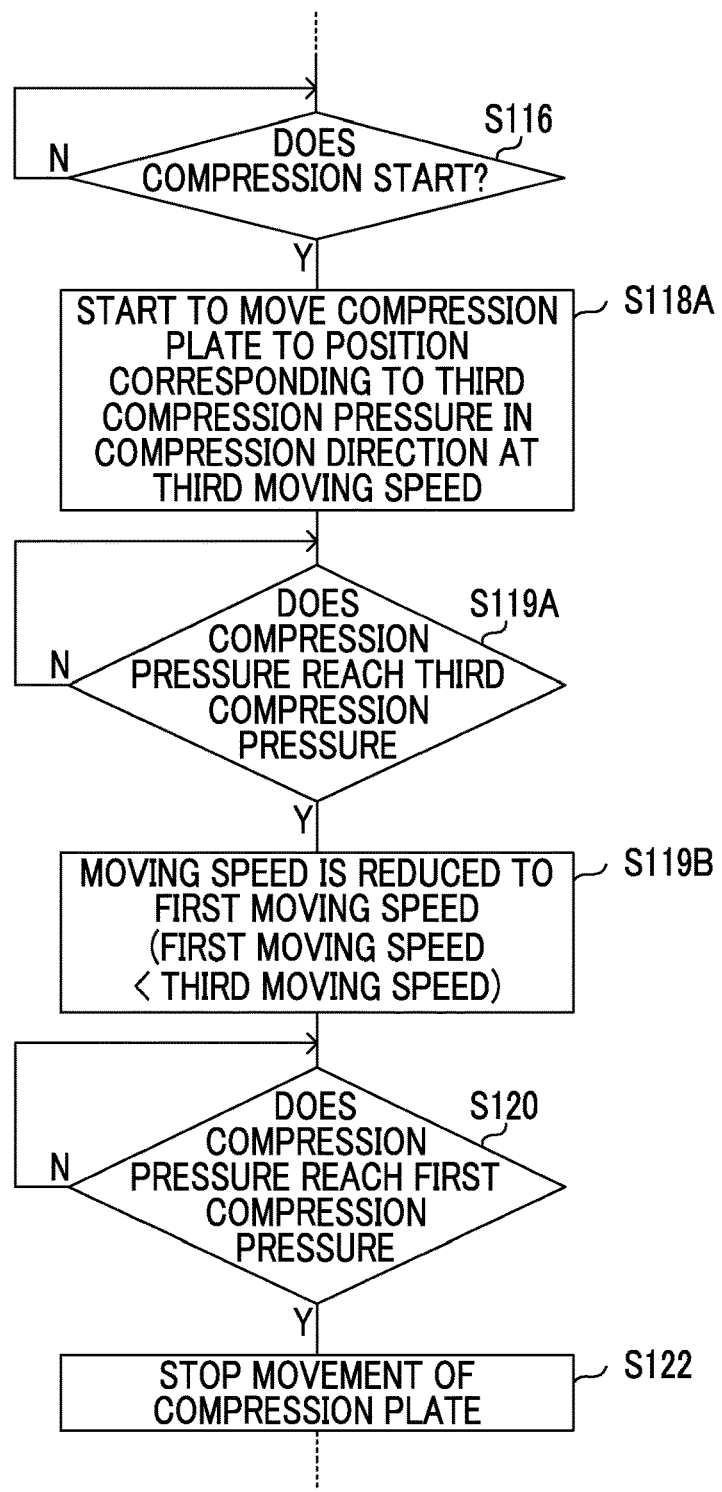
FIG. 35 is a flowchart illustrating an imaging process in a case in which the compression plate is moved at the moving speed illustrated in the timing chart of FIG. 34.

Therefore, as illustrated in FIG. 35, an imaging process performed by the control unit 40 of the mammography apparatus 12 according to this embodiment differs from the imaging process (see FIG. 9) performed by the control unit 40 of the mammography apparatus 12 according to the first embodiment in a process until the compression pressure reaches the first compression pressure M1 after the breast is compressed.

That is, the imaging process performed by the control unit 40 according to this embodiment differs from the imaging process according to the first embodiment in that it includes Step S118A instead of Step S118 according to the first embodiment and includes Step S119A and Step S119B before Step S120.

In a case in which the determination result in Step S116 is "Yes", in Step S118A, the control unit 40 directs the moving unit 30 to start to move the compression plate 28 from the initial position in the compression direction at the third moving speed S3.

Then, in Step S119A, the control unit 40 compares the compression pressure derived on the basis of the detection results of the pressure sensors 25 with the third compression pressure M3 set in the moving unit 30 and determines whether the compression pressure reaches the third compression pressure M3. In a case in which the compression pressure does not reach the third compression pressure M3, the determination result is "No" and the control unit 40 is in a standby state. On the other hand, in a case in which the compression pressure reaches the third compression pressure M3, the determination result is "Yes" and the process proceeds to Step S119B.

In Step S119B, the control unit 40 reduces the moving speed of the compression plate 28 by the moving unit 30 to the first moving speed S1.

As such, in a case in which the compression plate 28 is moved from the initial position to the position corresponding to the first compression pressure M1, the control unit 40 starts to move the compression plate 28 at the third moving speed S3 and reduces the moving speed to the first moving speed S1 after the compression pressure reaches the third compression pressure M3. Therefore, it is possible to reduce the total time required for imaging and to prevent the breast from being excessively compressed.

In the above-mentioned example, the case in which the moving speed of the compression plate 28 is reduced from the third moving speed S3 to the first moving speed S1 when the compression pressure derived on the basis of the detection results of the pressure sensors 25 reaches the third compression pressure M3 has been described. However, the time when the moving speed is reduced is not limited thereto. For example, a contact sensor, a pressure sensor, and a compression force sensor, such as a load cell, may be provided in the compression plate 28 and may detect the reaction force of the breast to the compression plate 28 and the moving speed may be reduced on the basis of the detection result. In addition, for example, when the compression of the breast starts, the compression plate 28 is inclined from the chest wall to the nipple of the subject. Therefore, a gyro sensor or a potentiometer may be provided and may detect the inclination of the compression plate 28 and the moving speed may be reduced on the basis of the detection result. For example, an optical camera may be provided and the contact between the breast and the compression plate 28 may be detected from the image of the side of the breast captured by the optical camera. The moving speed may be reduced at the time of the contact.

Figures 36, 37:
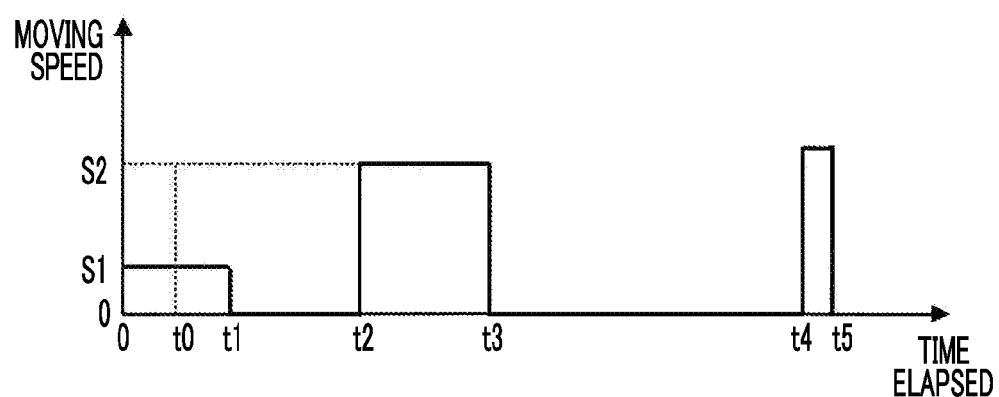
FIG. 36 is a timing chart illustrating another example of the moving speed of the compression plate in the mammography apparatus according to the tenth embodiment.
FIG. 37 is a diagram schematically illustrating an example of information indicating the correspondence relationship among the thickness of the breast, the second compression pressure, and a second moving speed.

The moving speed of the compression plate 28 moved from the initial position to the position corresponding to the first compression pressure M1 is not limited to the above-mentioned case. For example, in the first to seventh embodiments, the case in which the second moving speed S2 is lower than the first moving speed S1 in order to prevent, for example, deviation from the second compression pressure M2 has been described. However, as illustrated in FIG. 36, the second moving speed S2 may be higher than the first moving speed S1 in order to reduce the total time required for imaging, particularly, the time for which the breast is compressed.

For example, the control unit 40 of the mammography apparatus 12 may derive the second moving speed S2 according to the type of breast. For example, in a case in which the breast is thick, a reaction force is higher than that in a case in which the breast is thin, as described above. Therefore, the thickness of the decompressed breast is likely to return to the original value. For this reason, it is preferable that, as the thickness of the breast increases, the second moving speed S2 is reduced. In a case in which the control unit 40 derives the second moving speed S2 according to the thickness of the breast, as illustrated in FIG. 37, information 43A4 indicating the correspondence relationship among the thickness of the breast, the second compression pressure M2, the second moving speed S2 may be used instead of the information 43A1 indicating the correspondence relationship between the thickness of the breast and the second compression pressure M2 used in the second embodiment.

Figure 38:
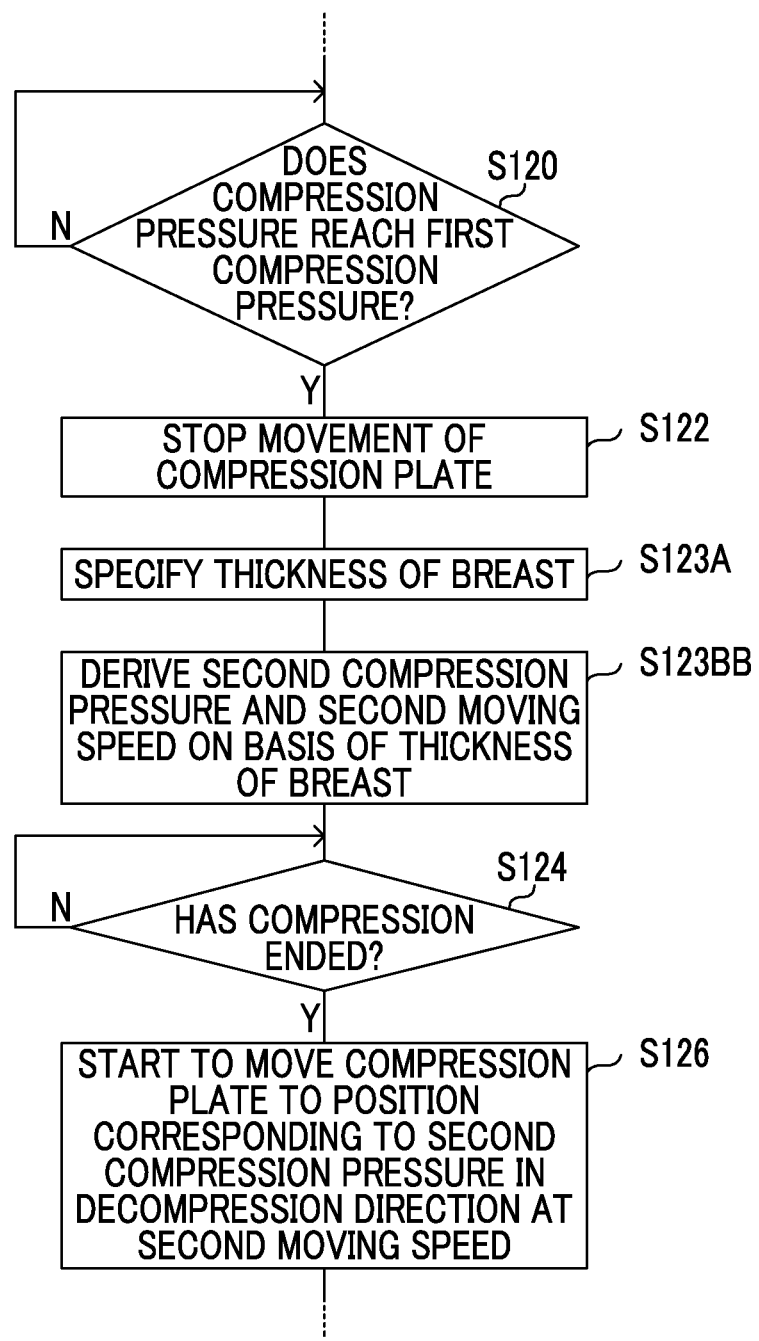
FIG. 38 is a flowchart illustrating an imaging process performed by the mammography apparatus according to the tenth embodiment in a case in which the second moving speed is derived on the basis of the thickness of the breast.

In the imaging process performed by the control unit 40, as illustrated in FIG. 38, Step S123BB is performed instead of Step S123B in the imaging process (see FIG. 14) according to the second embodiment. In Step S123BB, the control unit 40 derives the second compression pressure M2 and the second moving speed S2 on the basis of the thickness of the breast. Specifically, the control unit 40 derives the second compression pressure M2 and the second moving speed S2 on the basis of the thickness of the breast specified in Step S123A and the information 43A4 indicating the correspondence relationship among the thickness of the breast, the second compression pressure M2, and the second moving speed S2. Then, in Step S126, the control unit 40 starts to move the compression plate 28 in the decompression direction at the second moving speed S2 derived in Step S123BB.

In a case in which the second moving speed S2 is derived according to the type of breast, the second moving speed S2 may be derived according to, for example, the cup or size of the breast, similarly to the thickness of the breast. For example, in a case in which the cup is "AB", the second moving speed S2 may decrease. In a case in which the cup is "equal to or larger than E", the second moving speed S2 may increase. For example, in a case in which the size of the breast is "smaller" than normal, the second moving speed S2 may decrease. In a case in which the size of the breast is "larger" than normal, the second moving speed S2 may increase.

While the breast is moved to the position corresponding to the first compression pressure M1, for example, a compression force detection sensor (not illustrated) may detect a reaction force from the breast and the control unit 40 may derive the second moving speed S2 according to the magnitude of the detected reaction force, as described above. In this case, as described above, the control unit 40 derives a lower second moving speed S2 as the reaction force becomes higher.

As described above, the mammography apparatus 12 according to each of the above-described embodiments comprises the compression plate 28 that compresses the breast, the moving unit 30 that moves the compression plate 28 in the compression direction in which the breast is compressed and the decompression direction in which the breast is decompressed, the radiation source 24 that emits the radiation R, the pressure sensors 25 that measure the compression pressure of the compression plate 28 which is a compression force per unit area, and the control unit 40 that controls the moving unit 30 such that the compression plate 28 is moved to a first position where the compression pressure measured by the pressure sensors 25 is the first compression pressure in the compression direction and is then moved to a second position where the compression pressure measured by the pressure sensors 25 is the second compression pressure in the decompression direction and controls the radiation source 24 such that the radiation R is emitted to the breast in a state in which the compression plate 28 is located at the second position.

The first compression pressure is higher than the second compression pressure.

As such, the mammography apparatus 12 according to each of the above-described embodiments moves the compression plate 28 to control the compression pressure applied to the breast. Therefore, it is possible to effectively reduce the subject's pain caused by the compression of the breast by the compression plate 28.

As the integrated value of the compression pressure over the compression time increases, the subject's pain tends to increase. Therefore, the control unit 40 according to each of the above-described embodiments may control the time required to compress (press) or decompress the breast in order to reduce the subject's pain. For example, in a case in which the breast is compressed by the first compression pressure from the initial position, it is preferable that the integrated value of the compression pressure over the compression time is controlled to be equal to or less than 0.007 $N/mm^2 \cdot s$. For example, in a case in which the compression pressure is reduced from the first compression pressure to the second compression pressure, it is preferable that the integrated value of the compression pressure over the compression time is controlled to be equal to or less than 0.0014 $N/mm^2 \cdot s$.

Figure 39:
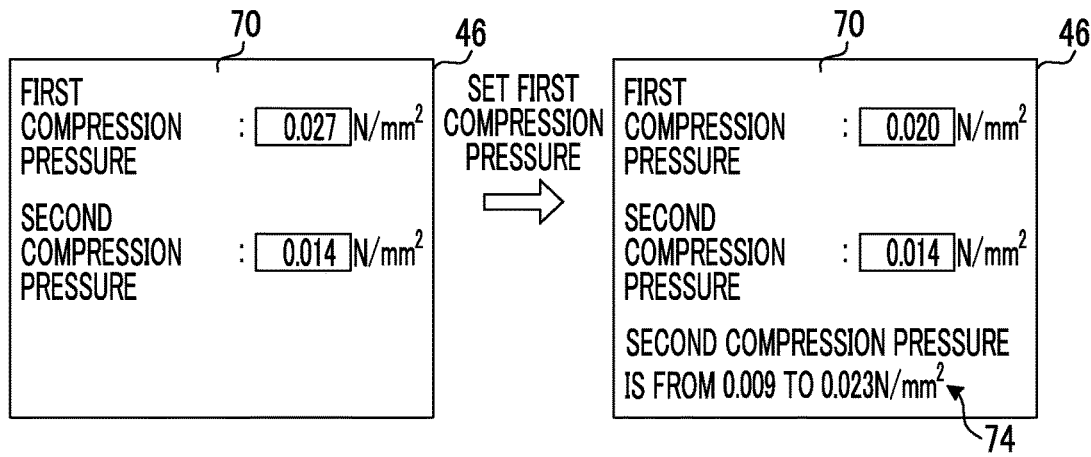
FIG. 39 is a diagram schematically illustrating an example of a compression pressure setting screen on which information indicating the range of the second compression pressure that can be set by the user, which is limited by a control unit in a case in which the user has set the first compression pressure, is displayed.

In each of the above-described embodiments, the case in which the user can set only one of the first compression pressure and the second compression pressure has been described. However, the user may set both the first compression pressure and the second compression pressure. In this case, first, when the user sets one of the compression pressures, preferably, the control unit 40 limits the range of the other compression pressure which can be set by the user according to the set compression pressure and presents information indicating the settable range to the user. FIG. 39 illustrates, for example, a state in which, in a case in which the user has set the first compression pressure, the control unit 40 limits the range of the second compression pressure that can be set by the user and displays information 74 indicating the settable range on the compression pressure setting screen 70. Here, it goes without saying that the settable range is based on the values of the first compression pressure and the second compression pressure described in the first embodiment.

The control unit 40 may stop the movement of the compression plate 28 before the compression pressure reaches the first compression pressure or the second compression pressure, in response to an instruction input by the user through, for example, the operation panel 46. Before the compression pressure reaches the first compression pressure, the control unit may move the compression plate 28 until the compression pressure reaches the second compression pressure, perform the emission of the radiation R, and acquire a radiographic image, in order to prevent re-imaging due to the insufficient expansion of the mammary gland. In addition, the control unit may perform the emission of the radiation R and acquire a radiographic image in a state in which the compression pressure in a stationary state is maintained, in terms of the subject's pain and imaging efficiency.

Figure 40:
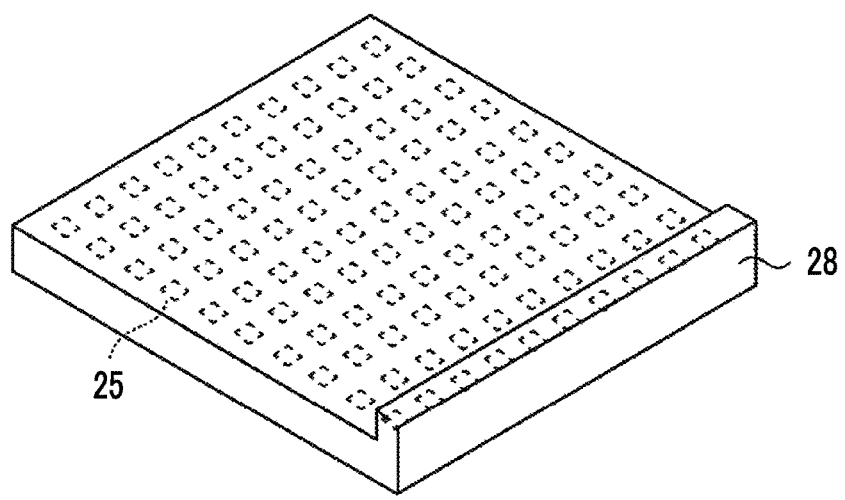
FIG. 40 is a diagram schematically an example of the state of pressure sensors provided on the compression plate.

In each of the above-described embodiments, the case in which the control unit 40 derives the compression pressure on the basis of the detection results of the pressure sensors 25 provided on the imaging surface 27 of the imaging stand 26 has been described. However, a method for deriving the compression pressure is not limited thereto. For example, as in the example illustrated in FIG. 40, n (50 in this embodiment) pressure sensors 25 may not be provided on the imaging surface 27, but may be provided on the compression plate 28. In addition, the size (area) of a contact region between the breast and the imaging surface 27 or the size (area) of a region of the breast which comes into contact with the pressure sensors 25 varies depending on the compression state of the breast. The size of each region increases with the compression of the breast. Therefore, it is preferable that the examples illustrated in FIG. 3 and FIG. 40 are combined with each other. That is, it is preferable that the pressure sensors 25 are provided on both the imaging surface 27 and the compression plate 28 and the compression pressure may be derived, using the detection results of the pressure sensors 25 provided on the imaging surface 27 and the detection results of the pressure sensors 25 provided on the compression plate 28.

The compression pressure may be derived, without using the pressure sensors 25. For example, as described above, the compression force detection sensor (not illustrated) is provided in the vicinity of the root of the compression plate 28 or in the vicinity of the root of the ball screw 37 and detects the compression force of the compression plate 28. In addition, an optical camera (not illustrated) that is provided, for example, in the vicinity of a collimator (not illustrated) of the radiation source 24 captures the image of the breast in synchronization with the time when the compression force detection sensor detects the compression force and the image analysis unit 32 according to the fourth embodiment performs the same image analysis as described above to derive the area of a region including the detected breast. Then, the control unit 40 may derive the compression pressure on the basis of the compression force detected by the compression force detection sensor and the derived area of the region including the breast.

A method for detecting the contact area between the breast and the imaging surface 27 or the compression plate 28 is not limited to the method using the image of the breast captured by the optical camera. For example, a sensor film in which a resistance value is changed by the contact of the breast, such as EXCLEAR (registered trademark) manufactured by FUJIFILM CORPORATION, may be provided in the imaging surface 27 or the compression plate 28, detect a region with which the breast comes into contact on the basis of the resistance value changed by the contact of the breast, and detect the contact area of the breast.

Figure 41:
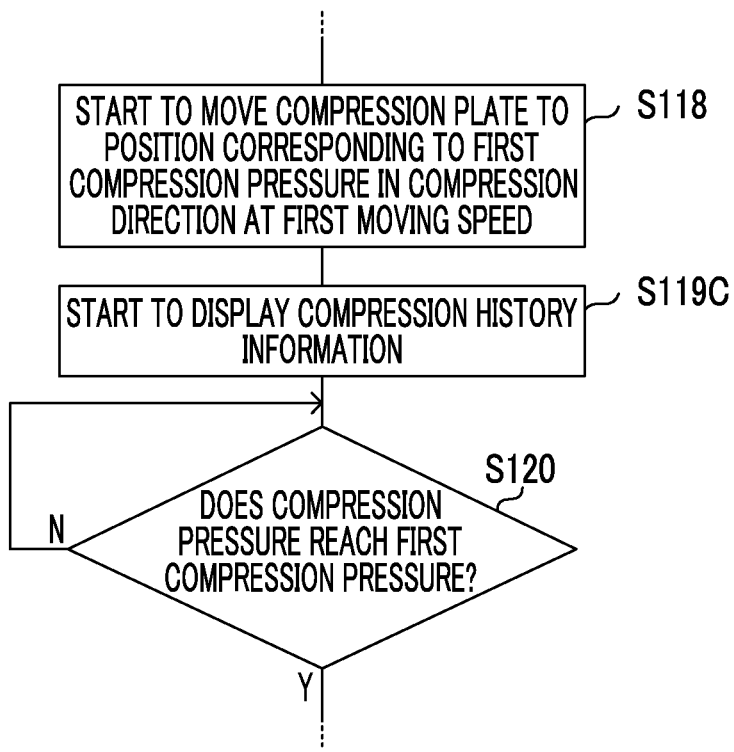
FIG. 41 is a flowchart illustrating an imaging process in a case in which compression history information is displayed.

The control unit 40 may display compression history information indicating the history of the compression pressure applied to the breast by the compression plate 28 on the display unit 58 of the console 16 or the operation panel 46 of the mammography apparatus 12. In this case, the control unit 40 may control the display of the compression history information. Therefore, for example, as illustrated in FIG. 41, in Step S118, the control unit 40 moves the compression plate 28 in the compression direction to start the compression of the breast. Then, in Step S119C, the control unit 40 starts the display of the compression history information.

Figure 42:
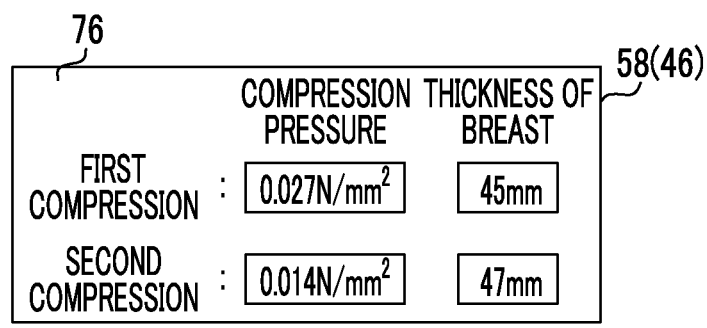
FIG. 42 is a diagram schematically illustrating an example of the compression history information.

For example, as illustrated in FIG. 42, the control unit 40 displays compression history information 76 including the first compression pressure as "first compression" and the second compression pressure as "second compression" on the display unit 58 or the operation panel 46. In an example of the compression history information 76 illustrated in FIG. 42, the thickness of the breast in the "first compression" and the "second compression" is also displayed. For example, in a case in which the thickness of the breast is detected as in the second embodiment, it is preferable that the thickness of the breast is also displayed as the compression history information 76. In this case, it is easy for the user to check the compression state of the breast.

Figures 43, 44:
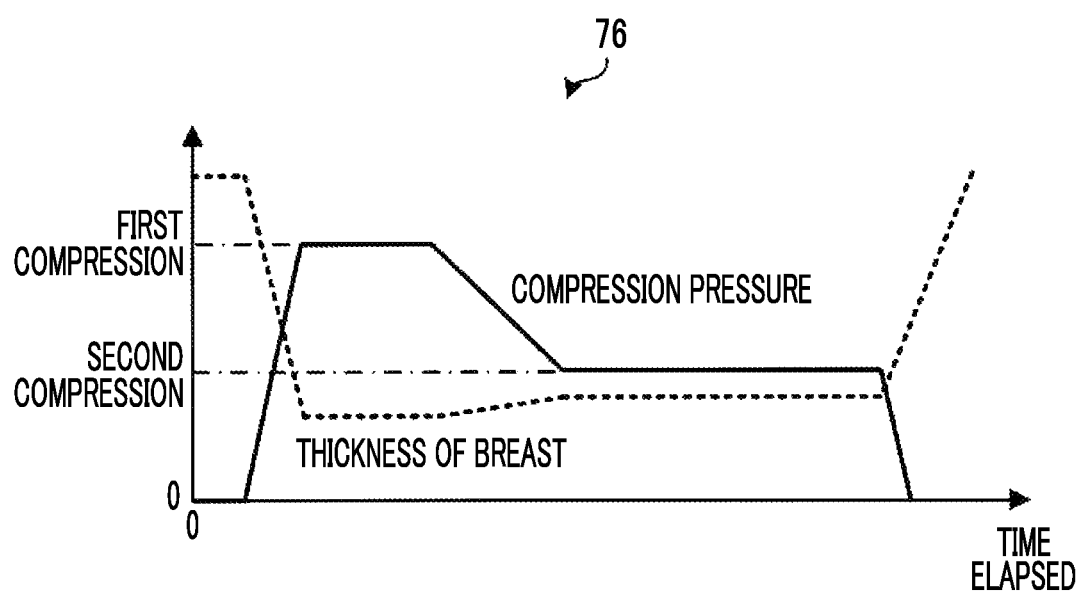
FIG. 43 is a diagram schematically illustrating another example of the compression history information.
FIG. 44 is a timing chart illustrating an example of a case in which the compression history information is displayed as a graph.

For example, as illustrated in FIG. 43, the current compression pressure or the current thickness of the breast may be displayed as the compression history information 76. FIG. 43 illustrates an example of the compression history information 76 that is displayed while the compression plate 28 is moved from the position corresponding to the first compression pressure to the position corresponding to the second compression pressure. In a case in which the compression history information 76 is displayed in this way, the control unit 40 may display, as the current compression force, the compression pressure which is repeatedly acquired at a predetermined interval.

As illustrated in a timing chart in FIG. 44, the compression history information 76 may be displayed as a graph indicating a variation in the compression pressure or a variation in the thickness of the breast. As such, a method for displaying the compression history information 76 is not particularly limited. The control unit 40 may store the compression history information 76 so as to be associated with the acquired radiographic image.

In each of the above-described embodiments, the case in which the control unit 40 of the mammography apparatus 12 functions as a control unit according to the invention has been described. However, the control unit 50 of the console 16 may have the functions of the control unit according to the invention. In this case, the console 16 functions as an example of a control device according to the invention.

In each of the above-described embodiments, the radiation R is not particularly limited. For example, X-rays or γ-rays may be applied.

In addition, for example, the structures and operations of the radiography system 10, the mammography apparatus 12, and the console 16 described in each of the above-mentioned embodiments are just an example and may be changed according to the situation, without departing from the scope and spirit of the invention.

EXPLANATION OF REFERENCES

10: radiography system
12: mammography apparatus
16: console
18: image storage system
22: radiation detector
24: radiation source
25: pressure sensor
26: imaging stand
27: imaging surface
28: compression plate
28A: attachment portion
28B: identification information
29: holding portion
30: moving unit
31: movement amount detection unit
32: image analysis unit
33: weight detection unit
35: identification sensor
36: connection portion
37: ball screw
38: motor
40, 50, 80: control unit
40A, 50A, 80A: CPU
40B, 50B, 80B: ROM
40C, 50C, 80C: RAM
41: two-stage compression prohibition information
42, 52, 82: storage unit
43: information indicating correspondence relationship between type of breast and second compression pressure
43A1 to 43A4: information indicating correspondence relationship between thickness of breast and second compression pressure
43B: information indicating correspondence relationship between cup of breast and second compression pressure
43C: information indicating correspondence relationship between size of breast and second compression pressure
43D: information indicating correspondence relationship between mammary gland density and second compression pressure
43E: information indicating correspondence relationship between hardness of breast and second compression pressure
43F: information indicating correspondence relationship between weight of breast and second compression pressure
44, 54, 84: I/F unit
46: operation panel
49, 63, 87: bus
56: display unit driving unit
58: display unit
60: operation input detection unit
62: operation unit
70: compression pressure setting screen
71: information indicating prohibition of setting
72: cup setting screen
74: information indicating settable range
76: compression history information
M1: first compression pressure
M2: second compression pressure
M3: third compression pressure
S1: first moving speed
S2: second moving speed
S3: third moving speed
R: radiation

What is claimed is:

1. A mammography apparatus comprising:
a compression plate that compresses a breast;
a moving unit that moves the compression plate in a compression direction in which the breast is compressed and a decompression direction in which the breast is decompressed;
a radiation source that emits radiation;
a measurement unit that measures a compression pressure which is a compression force of the compression plate per unit area; and
a control unit that controls the moving unit such that the compression plate is moved to a first position where the compression pressure measured by the measurement unit is a first compression pressure in the compression direction and is moved to a second position where the compression pressure measured by the measurement unit is a second compression pressure in the decompression direction and performs control such that the radiation is emitted from the radiation source to the breast in a state in which the compression plate is located at the second position.

2. The mammography apparatus according to claim 1, wherein the first compression pressure is higher than the second compression pressure.

3. The mammography apparatus according to claim 1, wherein the control unit further performs control such that a measurement result of the measurement unit is displayed on a display unit.

4. The mammography apparatus according to claim 1, further comprising:
a storage unit that stores the first compression pressure and the second compression pressure in advance.

5. The mammography apparatus according to claim 1, further comprising:
a storage unit that stores a plurality of second compression pressure candidates corresponding to the type of breast,
wherein the control unit uses a second compression pressure candidate selected from the plurality of second compression pressure candidates as the second compression pressure.

6. The mammography apparatus according to claim 5, further comprising:
an operation panel that is operable to set the type of breast.

7. The mammography apparatus according to claim 5, wherein the type of breast includes at least one of a thickness of the breast, a cup size of the breast, a size of the breast, a weight of the breast, a hardness of the breast, or mammary gland density.

8. The mammography apparatus according to claim 5, wherein, in a case in which the type of breast is a thickness of the breast, the candidate of the second compression pressure candidate decreases as the thickness of the breast decreases, or, in a case in which the type of breast is a cup size of the breast, the second compression pressure candidate decreases as the cup size of the breast decreases, or, in a case in which the type of breast is a size of the breast, the second compression pressure candidate decreases as the size of the breast decreases, or, in a case in which the type of breast is a weight of the breast, the second compression pressure candidate decreases as the weight of the breast decreases, or, in a case in which the type of breast is a mammary gland density, the second compression pressure candidate decreases as the mammary gland density increases.

9. The mammography apparatus according to claim 1, further comprising:
a compression pressure operation unit that is operated to set at least one of the first compression pressure or the second compression pressure.

10. The mammography apparatus according to claim 9, wherein, in a case in which the compression pressure operation unit is operated to set the first compression pressure, the control unit derives the second compression pressure according to the set first compression pressure and the type of breast.

11. The mammography apparatus according to claim 9, wherein, in a case in which the compression pressure operation unit is operated to set one of the first compression pressure and the second compression pressure, the magnitude of a compression pressure that can be set by an operation for the compression pressure operation unit as the other of the first compression pressure and the second compression pressure is limited.

12. The mammography apparatus according to claim 1, wherein the first compression pressure is equal to or greater than 0.018 $N/mm^2$ and the second compression pressure is in the range of 0.009 $N/mm^2$ to 0.023 $N/mm^2$.

13. The mammography apparatus according to claim 1, wherein, in a case in which a predetermined period of time has elapsed since the compression pressure measured by the measurement unit has reached the first compression pressure, the control unit controls the moving unit such that the movement of the compression plate in the decompression direction starts.

14. The mammography apparatus according to claim 1, wherein, in a case in which the compression pressure measured by the measurement unit reaches the first compression pressure, the control unit controls the moving unit such that the movement of the compression plate in the decompression direction starts.

15. The mammography apparatus according to claim 1, further comprising:
a movement instruction operation unit that is operated to input an instruction to move the compression plate to the second position,
wherein, in a case in which the movement instruction operation unit is operated to input an instruction to move the compression plate, the control unit controls the moving unit such that the movement of the compression plate to the second position starts.

16. The mammography apparatus according to claim 1, wherein, in a case in which the compression pressure measured by the measurement unit is equal to or greater than a predetermined value until the compression plate is moved to the first position, the control unit performs control such that a moving speed of the compression plate is reduced.

17. The mammography apparatus according to claim 1, further comprising:
a contact detection unit that detects whether the compression plate comes into contact with the breast,
wherein, in a case in which the contact detection unit detects the contact between the compression plate and the breast until the compression plate is moved to the first position, the control unit performs control such that a moving speed of the compression plate is reduced.

18. The mammography apparatus according to claim 1, wherein the control unit performs control such that a second moving speed of the compression plate in the decompression direction is lower than a first moving speed of the compression plate in the compression direction.

19. The mammography apparatus according to claim 18, wherein the control unit derives the second moving speed according to the type of breast.

20. The mammography apparatus according to claim 1, wherein the control unit performs control such that a second moving speed of the compression plate in the decompression direction is higher than a first moving speed of the compression plate in the compression direction.

21. The mammography apparatus according to claim 1, further comprising:
a prohibition information storage unit that stores prohibition information indicating the type of compression plate which is prohibited from being moved to the second position in the decompression direction; and a reading unit that reads identification information which identifies the type of compression plate and is provided in the compression plate, wherein the control unit prohibits control for moving the compression plate to the second position in the decompression direction, on the basis of the type of compression plate which is identified by the identification information read by the reading unit and the prohibition information stored in the prohibition information storage unit.

22. A control device comprising:

a receiving unit that receives a measurement result from a measurement unit that measures a compression pressure which is a compression force of a compression plate compressing a breast per unit area; and a control unit that controls a moving unit that moves the compression plate in a compression direction in which the breast is compressed and a decompression direction in which the breast is decompressed such that the compression plate is moved to a first position where the compression pressure received by the receiving unit is a first compression pressure in the compression direction and is moved to a second position where the compression pressure received by the receiving unit is a second compression pressure in the decompression direction and performs control such that radiation is emitted from a radiation source to the breast in a state in which the compression plate is located at the second position.

23. A mammography apparatus control method comprising:

receiving a measurement result from a measurement unit that measures a compression pressure which is a compression force of a compression plate compressing a breast per unit area;

controlling a moving unit that moves the compression plate in a compression direction in which the breast is compressed and a decompression direction in which the breast is decompressed such that the compression plate is moved to a first position where the received compression pressure is a first compression pressure in the compression direction;

controlling the moving unit such that the compression plate is moved to a second position where the received compression pressure is a second compression pressure in the decompression direction; and performing control such that radiation is emitted from a radiation source to the breast in a state in which the compression plate is located at the second position.

24. A non-transitory computer readable medium storing a program that causes a computer to execute a process to control a mammography apparatus, the process comprising:

receiving a measurement result from a measurement unit that measures a compression pressure which is a compression force of a compression plate compressing a breast per unit area;

controlling a moving unit that moves the compression plate in a compression direction in which the breast is compressed and a decompression direction in which the breast is decompressed such that the compression plate is moved to a first position where the received compression pressure is a first compression pressure in the compression direction;

controlling the moving unit such that the compression plate is moved to a second position where the received compression pressure is a second compression pressure in the decompression direction; and performing control such that radiation is emitted from a radiation source to the breast in a state in which the compression plate is located at the second position.

* * * * *